US012776061B2

(12) United States Patent
Beadle et al.

(10) Patent No.: US 12,776,061 B2
(45) Date of Patent: Oct. 27, 2026

(54) SYSTEMS AND METHODS FOR LOCATING USER INTERFACE LEAK

(71) Applicant: ResMed Sensor Technologies Limited, Dublin (IE)

(72) Inventors: Dylan Hermes da Fonseca Beadle, San Diego, CA (US); Luca Cerina, Dublin (IE); Varuni Lakshana Vithanage Fernando, Dublin (IE); Aoibhe Jacqueline Turner-Heaney, Dublin (IE); Katherine Molony, Dublin (IE); Liam Holley, Sydney (AU)

(73) Assignee: ResMed Sensor Technologies Limited, Dublin (IE)

(*) Notice: Subject to any disclaimer, the term of this patent is extended or adjusted under 35 U.S.C. 154(b) by 1003 days.

(21) Appl. No.: 17/928,488

(22) PCT Filed: May 28, 2021

(86) PCT No.: PCT/US2021/035006
§ 371 (c)(1),
(2) Date: Nov. 29, 2022

(87) PCT Pub. No.: WO2021/243293
PCT Pub. Date: Dec. 2, 2021

(65) Prior Publication Data

US 2023/0206486 A1 Jun. 29, 2023

Related U.S. Application Data

(60) Provisional application No. 62/704,826, filed on May 29, 2020.

(51) Int. Cl.
*G06T 7/73* (2017.01)
*A61M 16/00* (2006.01)
(Continued)

(52) U.S. Cl.
CPC ............ *G06T 7/73* (2017.01); *A61M 16/024* (2017.08); *A61M 16/0605* (2014.02);
(Continued)

(58) Field of Classification Search
CPC .......... A61M 16/0605; A61M 16/0644; A61M 16/0003; A61M 16/06; A61M 16/0666;
(Continued)

(56) References Cited

U.S. PATENT DOCUMENTS

2004/0074495 A1* 4/2004 Wickham .......... A61M 16/0858 128/204.23
2008/0060652 A1* 3/2008 Selvarajan ........ A61M 16/0683 128/206.21
(Continued)

FOREIGN PATENT DOCUMENTS

CN 201188051 Y 1/2009
EP 3167388 B1 1/2019
(Continued)

OTHER PUBLICATIONS

Eckert, Eric G., Location of Leaks in Pressurized Petroleum Pipelines by Means of Passive-Acoustic Sensing Methods, American Socieryt for Testing and Materials, Philadelphia, 1992 (Year: 1992).*
(Continued)

*Primary Examiner* — Victoria Murphy
*Assistant Examiner* — Sydney Reyes Russell
(74) *Attorney, Agent, or Firm* — Nixon Peabody LLP

(57) ABSTRACT

Detection of unintentional air leaks in a user interface (e.g., mask) of a respiratory therapy system (e.g., a positive air pressure device) is disclosed. One or more sensors (e.g., within a computing device, such as a smartphone) can be moved around relative to the user interface to determine a location and/or intensity of an air leak. The computing device can provide feedback regarding the location and/or
(Continued)

intensity of the air leak to facilitate the user locating the air leak, and thus correcting the air leak. In some cases, augmented reality annotations can be overlaid on an image (e.g., live image) of the user wearing the user interface to identify the location of the air leak. The system can automatically detect the type of user interface being used and can provide tailored guidance for reducing the air leaks.

22 Claims, 10 Drawing Sheets

(51) Int. Cl.

| | |
|---|---|
| ***A61M 16/06*** | (2006.01) |
| ***G01M 3/24*** | (2006.01) |
| ***G06T 19/00*** | (2011.01) |
| ***H04R 1/02*** | (2006.01) |

(52) U.S. Cl.
CPC ............. *G01M 3/24* (2013.01); *G06T 19/006* (2013.01); *H04R 1/028* (2013.01); *A61M 2205/15* (2013.01); *A61M 2205/3375* (2013.01); *A61M 2205/6063* (2013.01); *G06T 2207/10* (2013.01)

(58) Field of Classification Search
CPC .. A61M 16/0672; A61M 2205/502–52; A61M 2205/15; G06T 19/006; G06F 3/012; A61B 5/743; A61B 5/0077; G06V 40/165; G06V 40/171
See application file for complete search history.

(56) References Cited

U.S. PATENT DOCUMENTS

2008/0078248 A1* 4/2008 Farbarik ........... A61M 16/0051 73/613
2010/0180895 A1* 7/2010 Kwok .................. A61B 5/4812 128/204.23
2015/0133809 A1* 5/2015 Paul .................. A61M 16/0003 128/205.25
2015/0306330 A1* 10/2015 Richard ............... A61B 5/4818 348/77
2016/0092645 A1* 3/2016 Vlutters .................. G06F 30/20 715/771
2016/0243325 A1* 8/2016 Bowman ........... A61M 16/0069
2017/0203071 A1* 7/2017 Lawrenson ........... G06T 7/0014
2020/0121873 A1 4/2020 Hudson et al.
2020/0384229 A1* 12/2020 Lashinsky .............. G16H 50/50
2021/0038117 A1* 2/2021 Sadrnoori ............ A61B 5/0826

FOREIGN PATENT DOCUMENTS

JP 2016522935 A 8/2016
WO WO-02053217 A1 * 7/2002 .......... A61M 16/024
WO 2008/138040 A1 11/2008
WO WO-2010085895 A2 * 8/2010 .......... A61M 16/021
WO WO-2018050913 A1 * 3/2018 ........... A61B 5/0816
WO WO-2019006496 A1 * 1/2019 ............ A61M 16/06
WO 2020/104465 A2 5/2020

OTHER PUBLICATIONS

International Search Report in International Patent Application No. PCT/US2021/035006 mailed Aug. 24, 2021 (4 pp.).
Written Opinion in International Patent Application No. PCT/US2021/035006 mailed Aug. 24, 2021 (8 pp.).

* cited by examiner

SYSTEMS AND METHODS FOR LOCATING USER INTERFACE LEAK

CROSS-REFERENCE TO RELATED APPLICATIONS

The present application is the U.S. National Stage of International Patent Application No. PCT/US2021/035006, entitled "SYSTEMS AND METHODS FOR LOCATING USER INTERFACE LEAK" and filed May 28, 2021, which claims the benefit of U.S. Provisional Patent Application No. 62/704,826 filed May 29, 2020 and entitled "SYSTEMS AND METHODS FOR LOCATING USER INTERFACE LEAK," which is hereby incorporated by reference in its entirety.

TECHNICAL FIELD

The present disclosure relates to ventilation masks generally and more specifically to positive airway pressure mask fitting.

BACKGROUND

Many individuals suffer from conditions that can be remedied or improved through the use of various forms of respiratory therapy, such as continuous positive airway pressure (CPAP). Respiratory therapy generally includes the use of a respiratory therapy device (e.g., a positive airway pressure device, ventilator, etc.) fluidly coupled to a user interface (e.g., a mask) using a conduit (e.g., a hose). The efficacy of such therapies relies heavily on the use of a well-fit user interface. Different types of user interfaces are available to accommodate various users' physical features and personal preferences. Properly fitting a user interface may require a clinician visit and/or use of complicated and expensive fitting equipment. Further, many factors can affect the fit of a user interface during subsequent uses, such as changes in the users' physical features (e.g., swelling or hair growth), intentional or unintentional adjustments to the user interface or related equipment, impact or damage to the user interface or related equipment, and general wear and tear of user interface components (e.g., seals) over time.

As a result, user interfaces can leak air, thus reducing their efficacy. Further, air leaks can often lead to user discomfort and therapy non-compliance, such as if the user decides not to engage in the therapy due to the uncomfortable sensation or sound associated with the air leak. Air leaks are not generally visible to the user and some air leaks cannot be heard by a user. Users often have difficulty in locating and eliminating air leaks.

Some respiratory therapy devices are capable of detecting the existence of a leak somewhere downstream of the respiratory therapy device itself. However, detection of the existence of such a leak does not help inform where that leak may be located and does not help a user correct such a leak. In fact, due to the difficulties associated with locating air leaks around a user interface, users may incorrectly conclude the air leak is occurring within the conduit and/or the respiratory therapy device itself, which may lead to unnecessary expense to the user and/or manufacturer.

Therefore, there is a need for an easy-to-use tool to assist users in detecting and locating air leaks. There is a need for such a tool to guide the user in adjusting the user interface or accompanying equipment to reduce or minimize air leaks. There is a need for such a tool to help guide the user in achieving proper fit of a user interface.

SUMMARY

The term embodiment and like terms are intended to refer broadly to all of the subject matter of this disclosure and the claims below. Statements containing these terms should be understood not to limit the subject matter described herein or to limit the meaning or scope of the claims below. Embodiments of the present disclosure covered herein are defined by the claims below, supplemented by this summary. This summary is a high-level overview of various aspects of the disclosure and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this disclosure, any or all drawings and each claim.

Embodiments of the present disclosure include a method for detecting air leaks of a user interface worn by a user, comprising: receiving, at a computing device, a command to begin air leak detection of the user interface being worn by the user; receiving, from one or more sensors, acoustic data; identifying a location of an air leak using the received acoustic data; and presenting an indicator that is indicative of the location of the identified air leak.

In some cases, the identified air leak is an unintentional air leak. In some cases, the computing device is a mobile device. In some cases, the user interface is coupled to a respiratory therapy device via a conduit. In some cases, the method further comprises receiving an indication of a possible air leak from the respiratory therapy device. In some cases, the method further comprises presenting an instruction to set the respiratory therapy device to a preset flow rate, wherein receiving the acoustic data occurs while the respiratory therapy device is operating at the preset flow rate. In some cases, the method further comprises transmitting a flow rate command in response to receiving the command to begin air leak detection, wherein the flow rate command, when received by the respiratory therapy device, sets the respiratory therapy device to a preset flow rate, and wherein receiving the acoustic data occurs while the respiratory therapy device is operating at the preset flow rate.

In some cases, receiving the acoustic data comprises receiving the acoustic data from at least one microphone communicatively coupled to the computing device. In some cases, the method further comprises receiving movement data associated with movement of the computing device relative the user interface, wherein identifying the location of the air leak uses the acoustic data and the movement data. In some cases, identifying the location of the air leak comprises: accessing baseline acoustic data associated with intentional venting of the user interface; and filtering the baseline acoustic data to the acoustic data to identify the air leak. In some cases, identifying the location of the air leak comprises: analyzing the acoustic data to identify an acoustic characteristic associated with the air leak; and determining a relative strength of the air leak based on the acoustic characteristic. In some cases, the acoustic characteristic is a spectral frequency characteristic associated with the air leak.

In some cases, identifying the location comprises identifying a relative distance between the one or more sensors and the air leak. In some cases, presenting the indicator comprises presenting an indication of the relative distance between the computing device and the air leak. In some cases, the one or more sensors are positioned in or on the computing device. In some cases, presenting the indicator comprises generating at least one of an audio indicator, a visual indicator, or a haptic indicator. In some cases, the method further comprises presenting an instruction display, wherein the instruction display is indicative of a movement path for moving the computing device relative to the user interface. In some cases, presenting the instruction display comprises presenting feedback associated with the accuracy of the computing device's movement along the movement path. In some cases, the method further comprises receiving depth data associated with a distance between the computing device and the user interface, wherein identifying a location of the air leak further comprises: generating a three-dimensional mapping of the user interface relative to the computing device; and identifying the location of the air leak using the three-dimensional mapping of the user interface. In some cases, the acoustic data is associated with acoustic signals between 20 Hz and 20 kHz.

In some cases, the method further comprises receiving image data associated with the user interface, wherein presenting the indicator comprises presenting a visual indicator superimposed on the image data associated with the user interface. In some cases, receiving the image data associated with the user interface comprises capturing the image data using a camera of the computing device and displaying the image data on a display of the computing device. In some cases, the camera is a user-facing camera and the display is a user-facing display. In some cases, the image data is live image data.

In some cases, the method further comprises identifying guidance for reducing the air leak based on the location of the air leak; generating a guidance image based on the guidance for reducing the air leak; and presenting the guidance by superimposing the guidance image on the image data associated with the user interface. In some cases, the method further comprises identifying guidance for reducing the air leak based on the location of the air leak; and presenting the guidance using the computing device. In some cases, the method further comprises determining user interface identification information, wherein the user interface identification information is usable to identify a manufacturer of the user interface, a type of the user interface, or a model of the user interface, or any combination thereof, and wherein identifying guidance for reducing the air leak is based on the user interface identification information. In some cases, determining the user interface identification information is based on the received image data. In some cases, the method further comprises determining device identification information associated with the computing device, wherein the identification information is usable to identify a manufacturer of the computing device, a model of the computing device, or an identification of one or more sensors of the computing device, or any combination thereof; and calibrating the sensor data based on the device identification information. In some cases, the computing device is spaced apart from the user interface. In some cases, the computing device is a smartphone or tablet computer. In some cases, the method further comprises receiving thermal imaging data, wherein identifying the location of the air leak further comprises identifying the location using the thermal imaging data. In some cases, the method further comprises presenting an instruction to adjust the user interface, wherein adjustment of the user interface induces, increases, or reduces the air leak; and determining guidance to improve fit of the user interface based on identifying the location of the air leak. In some cases, the method comprises presenting the guidance.

Embodiments of the present disclosure include a system comprising: a control system including one or more processors; and a memory having stored thereon machine readable instructions; wherein the control system is coupled to the memory, and the method disclosed above is implemented when the machine executable instructions in the memory are executed by at least one of the one or more processors of the control system.

Embodiments of the present disclosure include a system for locating air leaks, the system including a control system having one or more processors configured to implement the method disclosed above.

Embodiments of the present disclosure include a computer program product comprising instructions which, when executed by a computer, cause the computer to carry out the method disclosed above. In some cases, the computer program product is a non-transitory computer readable medium.

BRIEF DESCRIPTION OF THE DRAWINGS

The specification makes reference to the following appended figures, in which use of like reference numerals in different figures is intended to illustrate like or analogous components.

DETAILED DESCRIPTION

Figure 1:
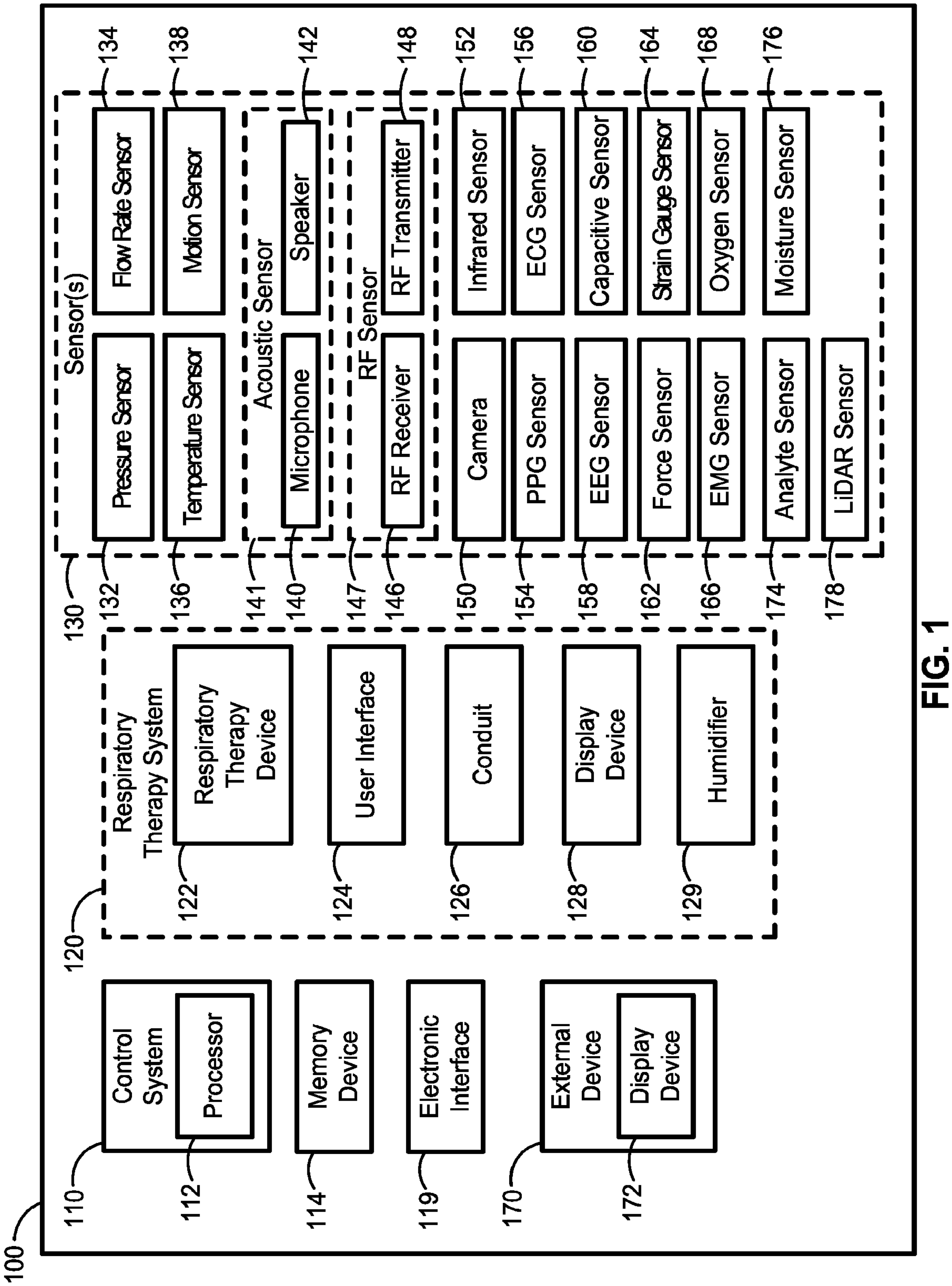
FIG. 1 is a functional block diagram of a system, according to certain aspects of the present disclosure.

Many individuals suffer from sleep-related and/or respiratory disorders. Examples of sleep-related and/or respiratory disorders include Periodic Limb Movement Disorder (PLMD), Restless Leg Syndrome (RLS), Sleep-Disordered Breathing (SDB) such as Obstructive Sleep Apnea (OSA), Central Sleep Apnea (CSA), and other types of apneas such as mixed apneas and hypopneas, Respiratory Effort Related Arousal (RERA), Cheyne-Stokes Respiration (CSR), respiratory insufficiency, Obesity Hyperventilation Syndrome (OHS), Chronic Obstructive Pulmonary Disease (COPD), Neuromuscular Disease (NMD), rapid eye movement (REM) behavior disorder (also referred to as RBD), dream enactment behavior (DEB), hyper tension, diabetes, stroke, insomnia, and chest wall disorders.

Obstructive Sleep Apnea (OSA) is a form of Sleep Disordered Breathing (SDB), and is characterized by events including occlusion or obstruction of the upper air passage during sleep resulting from a combination of an abnormally small upper airway and the normal loss of muscle tone in the region of the tongue, soft palate and posterior oropharyngeal wall. More generally, an apnea generally refers to the cessation of breathing caused by blockage of the air (Obstructive Sleep Apnea) or the stopping of the breathing function (often referred to as Central Sleep Apnea). Typically, the individual will stop breathing for between about 15 seconds and about 30 seconds during an obstructive sleep apnea event.

Other types of apneas include hypopnea, hyperpnea, and hypercapnia. Hypopnea is generally characterized by slow or shallow breathing caused by a narrowed airway, as opposed to a blocked airway. Hyperpnea is generally characterized by an increase depth and/or rate of breathing. Hypercapnia is generally characterized by elevated or excessive carbon dioxide in the bloodstream, typically caused by inadequate respiration.

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterized by repetitive de-oxygenation and re-oxygenation of the arterial blood.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common, such as increased resistance to air movement, extended expiratory phase of respiration, and loss of the normal elasticity of the lung.

Neuromuscular Disease (NMD) encompasses many diseases and ailments that impair the functioning of the muscles either directly via intrinsic muscle pathology, or indirectly via nerve pathology. Chest wall disorders are a group of thoracic deformities that result in inefficient coupling between the respiratory muscles and the thoracic cage.

A Respiratory Effort Related Arousal (RERA) event is typically characterized by an increased respiratory effort for ten seconds or longer leading to arousal from sleep and which does not fulfill the criteria for an apnea or hypopnea event. RERAs are defined as a sequence of breaths characterized by increasing respiratory effort leading to an arousal from sleep, but which does not meet criteria for an apnea or hypopnea. These events must fulfil both of the following criteria: (1) a pattern of progressively more negative esophageal pressure, terminated by a sudden change in pressure to a less negative level and an arousal, and (2) the event lasts ten seconds or longer. In some implementations, a Nasal Cannula/Pressure Transducer System is adequate and reliable in the detection of RERAs. A RERA detector may be based on a real flow signal derived from a respiratory therapy device. For example, a flow limitation measure may be determined based on a flow signal. A measure of arousal may then be derived as a function of the flow limitation measure and a measure of sudden increase in ventilation. One such method is described in WO 2008/138040, assigned to ResMed Ltd., the disclosure of which is hereby incorporated by reference herein in its entirety.

These and other disorders are characterized by particular events (e.g., snoring, an apnea, a hypopnea, a restless leg, a sleeping disorder, choking, an increased heart rate, labored breathing, an asthma attack, an epileptic episode, a seizure, or any combination thereof) that occur when the individual is sleeping.

The Apnea-Hypopnea Index (AHI) is an index used to indicate the severity of sleep apnea during a sleep session. The AHI is calculated by dividing the number of apnea and/or hypopnea events experienced by the user during the sleep session by the total number of hours of sleep in the sleep session. The event can be, for example, a pause in breathing that lasts for at least 10 seconds. An AHI that is less than 5 is considered normal. An AHI that is greater than or equal to 5, but less than 15 is considered indicative of mild sleep apnea. An AHI that is greater than or equal to 15, but less than 30 is considered indicative of moderate sleep apnea. An AHI that is greater than or equal to 30 is considered indicative of severe sleep apnea. In children, an AHI that is greater than 1 is considered abnormal. Sleep apnea can be considered "controlled" when the AHI is normal, or when the AHI is normal or mild. The AHI can also be used in combination with oxygen desaturation levels to indicate the severity of Obstructive Sleep Apnea.

Many individuals suffering from any combination of the aforementioned conditions may make use of respiratory therapy, such as continuous positive airway pressure (CPAP). Respiratory therapy generally includes the use of a respiratory therapy device (e.g., a positive airway pressure device, ventilator, etc.) fluidly coupled to a user interface (e.g., a mask) using a conduit (e.g., a hose). Since the efficacy of respiratory therapy relies heavily on the use of a well-fit user interface, it can be desirable to detect and/or predict ill-fitting user interfaces, such as user interfaces with unintentional air leaks.

Certain aspects and features of the present disclosure relate to detection of unintentional air leaks in a user interface (e.g., mask) of a respiratory therapy system (e.g., a positive air pressure system). One or more sensors (e.g., within a computing device, such as a smartphone) can be moved around relative to the user interface to determine a location and/or intensity of an air leak. The computing device can provide feedback regarding the location and/or intensity of the air leak to facilitate the user locating the air leak, and thus correcting the air leak. In some cases, augmented reality annotations can be overlaid on an image (e.g., live image) of the user wearing the user interface to identify the location of the air leak. The system can automatically detect the type of user interface being used and can provide tailored guidance for reducing the air leak.

Certain aspects and features of the present disclosure relate to air leaks associated with vented user interfaces, although that need not always be the case. Vented user interfaces permit air to escape the user interfaces at certain locations (e.g., vent locations). In use, a user undergoing respiratory therapy may inhale air from the respiratory therapy device, but may exhale some of the exhaled breath through the vents of the user interface. The exhaled breath through the vent may be an intentional air leak. While these intentional air leaks may be desirable, unintentional air leaks are not desirable, and can negatively affect the respiratory therapy and/or the user's comfort and/or compliance with the respiratory therapy. Unintentional air leaks are often located around the edge or periphery of the user interface, but can also be located at any sealing interface of the user interface (e.g., a sealing interface between the user interface and the conduit supplying the user interface, or a sealing interface between a frame and cushion of the user interface, etc.).

For the purposes of this disclosure, the term air leak will generally refer to an unintentional air leak. Additionally, the term air leak can include a probable or purported air leak, as appropriate. For example, disclosure related to the detection of an air leak and/or annotation of the location of an air leak can be inclusive of detection/annotation of an actual air leak and/or detection/annotation of a probable or purported air leak. Additionally, while many features and aspects of the present disclosure are described with reference to an air leak, it will be understood that multiple air leaks can be handled simultaneously.

As disclosed herein, various sensors and/or combinations of sensors can be used to determine a location of an air leak. As used herein, determination of a location of an air leak can include determination of a 2D or 3D location of an air leak (e.g., a specific location in a 2D or 3D mapping, or a relative location in a 2D or 3D space relative to one or more sensors, such as a vector). In some cases, determination of location of an air leak can include determination of a 1D location of an air leak, which can be a relative intensity of an air leak as measured by one or more sensors (e.g., a 1-dimensional indication of distance (e.g., radial distance) of the air leak from the one or more sensors).

In some cases, the types of sensors available for the air leak detection process can be based on the sensors available in the device(s) being used. For example, when a computing device such as a smartphone is used, the types of sensors available for air leak detection can be based on the sensors present in or otherwise coupled to the computing device. Further, the specifications of different versions of the same sensor (e.g., different microphones) can differ. In some cases, the process can include receiving identification information associated with the one or more sensors (e.g., identification information associated with the computing device), which can be used to adjust the air leak detection process. In some cases, the one or more sensor can be calibrated based on the identification information associated with the one or more sensors. Identification information associated with the one or more sensors can be obtained manually by the user (e.g., via providing the information using an input interface) or can be automatically obtained (e.g., via automatic detection of the computing device).

In some cases, a microphone can be used to detect sound associated with an air leak. The sound associated with the air leak may be audible sound or may be non-audible sound (e.g., ultrasonic). However, certain aspects and features of the present disclosure can be especially useful in the detection of air leaks associated with audible sound (e.g., between 20 Hz and 20 kHz) or near-ultrasonic sound (e.g., at or below 24 kHz, such as between 22-24 kHz, or otherwise at or below half of the maximum sampling rate of the hardware associated with the microphone). Air leaks associated with higher frequencies may by sufficiently small to not substantially affect the types of respiratory therapy disclosed herein. In some cases, sound associated with the air leak can exhibit a recognizable frequency fingerprint, which can be separated from intentional air leaks (e.g., venting) and other noise. In some cases, intentional leaks and/or other noise can be detected for a period of time to use as a basis for filtering out the sound not associated with the air leak (e.g. unintentional air leak). In an example, a user can be instructed to record sound across multiple breaths (e.g., 2-6 breaths). In such an example, intentional leaks and/or other noise may be easily identified as consistent noises, which can be filtered out, leaving the intentional leaks. In some cases, the recording of sound associated with intentional leaks can be performed at a low pressure (e.g., a relatively low pressure from the respiratory therapy device) to minimize sound associated with the unintentional leaks, thus providing baseline acoustic data associated with intentional leaks, which can be filtered out from subsequent acoustic data. The subsequent acoustic data can be recorded at higher pressure, in which case the unintentional leaks may be more noticeable.

Through experimentation, it has been determined that non-leaking user interfaces produce a sound pattern that is associated primarily with the respiratory therapy device (e.g., the air blower in the respiratory therapy device). Generally, such sound patterns show spectral peaks near the power-line frequency (e.g., at or around 50 Hz or 60 Hz). However, when a user interface is leaking unintentionally, turbulence in the air flow can cause a noise that is in a different spectrum, potentially in the audible spectrum. In some cases, the spectral peaks associated with an air leak can be around 100 Hz and 1000 Hz. In some cases, noise associated with an air leak can have a spectral shape or pattern that is differentiable from noise associated with intentional air leaks or other expected noises.

In some cases, by moving the microphone around relative to the user interface, the air leak's location can be determined. In some cases, an air leak's location can be determined based on a sensed intensity of the sound waves associated with the air leak. Thus, by moving the microphone around, the air leak's location is likely nearest where the associated sound intensity is the highest. In some cases, feedback can be provided (e.g., haptic, audible, or visual feedback) to indicate the intensity of the sound waves associated with the air leak. In some cases, measurements from multiple positions can be used to determine a location of an air leak, such as through triangulation or beamforming. In some cases, the user can be directed to move the computing device along a desired path to facilitate sampling from numerous useful positions, thus facilitating identification of the location of the air leak. Motion sensors and/or cameras can be used to ensure the computing device is being moved along the desired path. In some cases, the use of multiple sensors at different positions (e.g., microphones in a smartphone and/or microphones in headphones coupled to the smartphone) can be used simultaneously to determine a location of an air leak (e.g., via triangulation or beamforming).

In some cases, a thermal sensor can be used to detect skin temperature on the face of the user wearing the user interface. Small instances of cooler skin temperature near the periphery of the user interface can be indicative of an air leak.

In some cases, a camera can be used to capture image data of the user wearing the user interface. In some cases, this image data can be overlaid with annotations to provide real-time feedback to the user, such as in the form of an augmented reality video. Annotations can indicate the location of the air leak, an intensity of an air leak, and other information. In some cases, guidance can be provided to make adjustments to help identify/locate an air leak or to minimize the air leak, such as by making adjustments to the user interface. Adjustments can be small (e.g., push on a particular side of the user interface) or larger (e.g., tighten a particular strap coupled to the user interface). In an example, if pushing on one area of a mask causes sounds presumed to be associated with an unintentional air leak to decrease or disappear, such adjustments can be used to confirm that the presumed unintentional air leak is indeed an unintentional air leak.

In some cases, a depth sensor (e.g., one or more cameras, an IR camera associated with an IR projector, or the like) can be used to determine depth information associated with the user wearing the user interface. In such cases, the depth information can be used to facilitate identification of the location of the air leak, such as to generate a 2D or 3D mapping of the user interface being worn by the user and/or to more accurately identify the position of the computing device relative the user interface being worn by the user. In some cases, depth data can be inferred and/or approximated through the use of a camera or other device capable of detecting certain known or expected elements of the user and/or user interface. For example, use of a camera to identify a user's nose and ears can be used to approximate depth data for different points on the user interface. In another example, knowledge of the type (e.g. full face, nasal, or nasal pillow, etc.), and optionally model (e.g. AirFit™ F20, or AirFit™ N30 (both from ResMed), etc.), of user interface being worn by the user can be used to approximate depth data for different points on the user interface based on known measurements of the user interface.

In some cases, the guidance can be based on the actual type, and optionally model, of user interface being used by the user. The type, and optionally model, can be determined through user interface identification information, which can be user-provided, previously stored, or dynamically obtained. For example, user interface identification information can be dynamically obtained by the one or more sensors detecting the user interface identification information or detecting features indicative of the user interface identification information.

Additionally, in some cases, user interface identification information can be used to obtain information about the user interface that can be used to facilitate generating a 2D or 3D mapping of the user interface and/or can be used to facilitate identifying and/or excluding intentional noise associated with operation of the user interface without air leaks. For example, knowledge of a type, and optionally model, of user interface can provide information about the location of vents and/or the audio frequency patterns exhibited by intentional air leaks at those vents. In such cases, this information can be used to facilitate detection of unintentional air leaks and/or detection of the location of unintentional air leaks.

In some cases, an image of the user interface can be used to identify the user interface by comparing it to a comparison database. The comparison database can include known images and/or geometric models (e.g., 2D and/or 3D geometric models) of a range of user interfaces. For example a set of landmarks, curves, or edges, or other features in a 2D or 3D image may be compared with features in a database of 2D or 3D geometrical models of user interface to be identified. Statistical approaches such as joint probability, or machine learning methods such as a Support Vector Machine, or other methods may be used to predict the user interface in use in an acquired 2D or 3D image. The user interface predicted to be in use based on the acquired image data can be known as a matching user interface.

In some cases, regions of 2D or 3D images or models of user interfaces may be classified as regions of interest for leak analysis. Regions of interest may be predetermined and assigned to regions of models of user interfaces and stored in a database, or they may be learned over a period of time by compiling data that combines geometric information such as that from a camera image or geometric model, with information indicating leak, such as that from an acoustic sensor, or flow sensor, or other sensor, in one or more devices. In some cases, regions of interest for leak analysis may be assigned to models or images as being regions that are known to be or suspected to be surfaces that are typically intended to be air sealing surfaces between the pressurized air within the user interfaces and the wearer of the user interfaces. Additionally, regions of interest may include regions that are proximal to regions that are designated as sealing surfaces.

Once a region of interest is identified, it can be used to help inform and/or limit identification of an air leak. In an example, suspected air leaks identified from acoustic data that lie outside of an identified region of interest can be automatically eliminated as being intentional air leaks. In another example, the estimated location of a suspected air leak can be modified and/or more accurately pinpointed based on an identified region of interest. In such an example, analysis of acoustic data may identify a location of an air leak within a 4 cm diameter circle, but if only a small portion of that circle lies within an identified region of interest, the location of the air leak may be improved to be only the region of intersection between the region of interest and the 4 cm diameter circle. In some cases, an identified region of interest can be used to facilitate presentation of a suspected air leak. For example, if a suspected air leak is located within an identified region of interest, the indicator presented to indicate the location of the air leak can include a highlighting or other indication of the entire region of interest in which the suspected air leak is located. The region of interest can also be used in other ways and for other purposes.

In some cases, analysis of acoustic signals can be used to identify sounds that contain features that are associated with features that are common to noise created by air leaking. For example, there may be periods of continuous noise which is highly random in nature. In some cases, the analyses may compare features in different frequency ranges, such as comparing features below 1000 Hz with features above 1000 Hz. In some cases, features to be compared may include a measure of whiteness (e.g., power distribution across frequency ranges), amplitude, variation in amplitude, as well as variation in feature(s) over different length time windows.

In some cases, an array of sensors, such as microphones, with known position relative to each other or some other (known) frame of reference, and relative to a 2D or 3D image sensing transducer or system, may be used to record a number of signals to which acoustic beamforming or holography techniques may be applied to identify regions on an image or model within a particular amplitude range, or with a character of noise. In some cases, beamforming or holography analysis may be constrained to only analyzing regions that have been determined to be of interest for leak analysis. In this way, the amount of processing required can be significantly reduced compared with traditional acoustic source location processing techniques.

In some cases, novel methods of acoustic source location techniques may be used, such as in the case where there is a continuous leak sound source. Rather than traditional beamforming that triangulates between multiple sensors and a source, a novel method of triangulation to the source with one or more microphones may be employed, and which may be moved to different locations (e.g., by slowly moving the one or more microphones, optionally housed in a smartphone, with respect to the user interface, such as around the user interface). In such cases, it can be important to accurately know the location of the microphone (e.g., relative to the user interface). In some cases, the frame of the sensors may be determined by, for example, fitting a special model of the 3D geometry of an identified user interface, with a live capture of a 2D or 3D image containing the user interfaces, such that the orientation of the image and its scale give the angle and distance from the user interfaces to the microphone(s). In some cases, a model of the lens and/or image sensor system may be used that will influence the scale to distance transform. In some cases, because the different microphone locations may not be recording exactly the same source time signal (as would traditionally be the case with an array of microphones), rather than triangulating with delay and sum of time signals, one method of estimating source location can include calculating the spectrum and tracking the unwrapped phase of dominant spectral components of the leak sound. In some cases, one may determine (from the fitted image/3D model) how far the sensor system has moved from the source, then combine an estimate of speed of sound with the phase shift to more accurately localize the position of the source sound. In some cases, sources that are located in regions with low expectation of leak can be excluded to reduce the probability of unknowingly identifying 'ghost' images of the source.

In some cases, detection of air leaks can be indicative of equipment (e.g., user interfaces, seals, or other related equipment) that may be wearing and may be in need of replacement or repair. In some cases, guidance provided to the user can include a recommendation to repair or replace such equipment. For example, a recommendation to replace a seal can include a link or other information to facilitate purchasing the replacement seal. In some cases, guidance can include a recommendation to use a different type and/or model of user interface.

In some cases, an air leak detection process can first involve detecting whether or not a leak is present. Detection of whether or not a leak is present can include analyzing acoustic data to identify a frequency pattern indicative of a leak or receiving indication of a leak from a respiratory therapy device (e.g., a positive airway pressure device, or ventilator, etc.). After the presence of an air leak has been detected, the user can be instructed to move the computing device along a path or otherwise position the one or more sensors to identify the location of the air leak.

In some cases, certain aspects and features of the present disclosure permit air leaks to be identified and located without the need for sensors placed within a user interface itself.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative embodiments but, like the illustrative embodiments, should not be used to limit the present disclosure. The elements included in the illustrations herein may not be drawn to scale.

FIG. 1 is a functional block diagram of a system 100, according to certain aspects of the present disclosure. The system 100 includes a control system 110, a memory device 114, an electronic interface 119, one or more sensors 130, and one or more external devices 170 (e.g., user devices, such as a computing device). In some implementation, the system 100 further optionally includes a respiratory therapy system 120. The system 100 can be used to detect, identify, and offer corrective guidance for a leak in user interface 124, as disclosed in further detail herein.

The control system 110 includes one or more processors 112 (hereinafter, processor 112). The control system 110 is generally used to control (e.g., actuate) the various components of the system 100 and/or analyze data obtained and/or generated by the components of the system 100. The processor 112 can be a general or special purpose processor or microprocessor. While one processor 112 is shown in FIG. 1, the control system 110 can include any suitable number of processors (e.g., one processor, two processors, five processors, ten processors, etc.) that can be in a single housing, or located remotely from each other. The control system 110 can be coupled to and/or positioned within, for example, a housing of the external device 170, and/or within a housing of one or more of the sensors 130. The control system 110 can be centralized (within one such housing) or decentralized (within two or more of such housings, which are physically distinct). In such implementations including two or more housings containing the control system 110, such housings can be located proximately and/or remotely from each other.

The memory device 114 stores machine-readable instructions that are executable by the processor 112 of the control system 110. The memory device 114 can be any suitable computer readable storage device or media, such as, for example, a random or serial access memory device, a hard drive, a solid state drive, a flash memory device, etc. While one memory device 114 is shown in FIG. 1, the system 100 can include any suitable number of memory devices 114 (e.g., one memory device, two memory devices, five memory devices, ten memory devices, etc.). The memory device 114 can be coupled to and/or positioned within a housing of the respiratory therapy device 122, within a housing of the external device 170, within a housing of one or more of the sensors 130, or any combination thereof. Like the control system 110, the memory device 114 can be centralized (within one such housing) or decentralized (within two or more of such housings, which are physically distinct). In some implementations, the memory device 114 stores a user profile associated with the user. The user profile can include, for example, demographic information associated with the user, biometric information associated with the user, medical information associated with the user, self-reported user feedback, sleep parameters associated with the user (e.g., sleep-related parameters recorded from one or more earlier sleep sessions), or any combination thereof. The demographic information can include, for example, information indicative of an age of the user, a gender of the user, a race of the user, a geographic location of the user, a relationship status, a family history of insomnia or sleep apnea, an employment status of the user, an educational status of the user, a socioeconomic status of the user, or any combination thereof. The medical information can include, for example, information indicative of one or more medical conditions associated with the user, medication usage by the user, or both. The medical information data can further include a multiple sleep latency test (MSLT) result or score and/or a Pittsburgh Sleep Quality Index (PSQI) score or value. The self-reported user feedback can include information indicative of a self-reported subjective sleep score (e.g., poor, average, excellent), a self-reported subjective stress level of the user, a self-reported subjective fatigue level of the user, a self-reported subjective health status of the user, a recent life event experienced by the user, or any combination thereof.

The electronic interface 119 is configured to receive data (e.g., physiological data, acoustic data, or image data) from the one or more sensors 130 such that the data can be stored in the memory device 114 and/or analyzed by the processor 112 of the control system 110. The electronic interface 119 can communicate with the one or more sensors 130 using a wired connection (e.g., a bus, such as an internal bus or an external bus) or a wireless connection (e.g., using an RF communication protocol, a Wi-Fi communication protocol, a Bluetooth communication protocol, over a cellular network, etc.). The electronic interface 119 can include an antenna, a receiver (e.g., an RF receiver), a transmitter (e.g., an RF transmitter), a transceiver, or any combination thereof. The electronic interface 119 can also include one or more processors and/or one or more memory devices that are the same as, or similar to, the processor 112 and the memory device 114 described herein. In some implementations, the electronic interface 119 is coupled to or integrated in the external device 170. In other implementations, the electronic interface 119 is coupled to or integrated (e.g., in a housing) with the control system 110 and/or the memory device 114.

As noted above, in some implementations, the system 100 optionally includes a respiratory therapy system 120. The respiratory therapy system 120 can include a respiratory pressure therapy device 122 (referred to herein as respiratory therapy device 122), a user interface 124 (also referred to as a mask or a patient interface), a conduit 126 (also referred to as a tube or an air circuit), a display device 128, a humidifier 129, or any combination thereof. In some implementations, the control system 110, the memory device 114, the display device 128, one or more of the sensors 130, and the humidifier 129 are part of the respiratory therapy device 122. Respiratory pressure therapy refers to the application of a supply of air to an entrance to a user's airways at a controlled target pressure that is nominally positive with respect to atmosphere throughout the user's breathing cycle (e.g., in contrast to negative pressure therapies such as the tank ventilator or cuirass). The respiratory therapy system 120 is generally used to treat individuals suffering from one or more sleep-related respiratory disorders (e.g., obstructive sleep apnea, central sleep apnea, or mixed sleep apnea).

The respiratory therapy system 100 can be used, for example, as a ventilator or as a positive airway pressure (PAP) system, such as a continuous positive airway pressure (CPAP) system, an automatic positive airway pressure system (APAP), a bi-level or variable positive airway pressure system (BPAP or VPAP), or any combination thereof. The CPAP system delivers a predetermined air pressure (e.g., determined by a sleep physician) to the user. The APAP system automatically varies the air pressure delivered to the user based on, for example, respiration data associated with the user. The BPAP or VPAP system is configured to deliver a first predetermined pressure (e.g., an inspiratory positive airway pressure or IPAP) and a second predetermined pressure (e.g., an expiratory positive airway pressure or EPAP) that is lower than the first predetermined pressure.

Figure 2A:
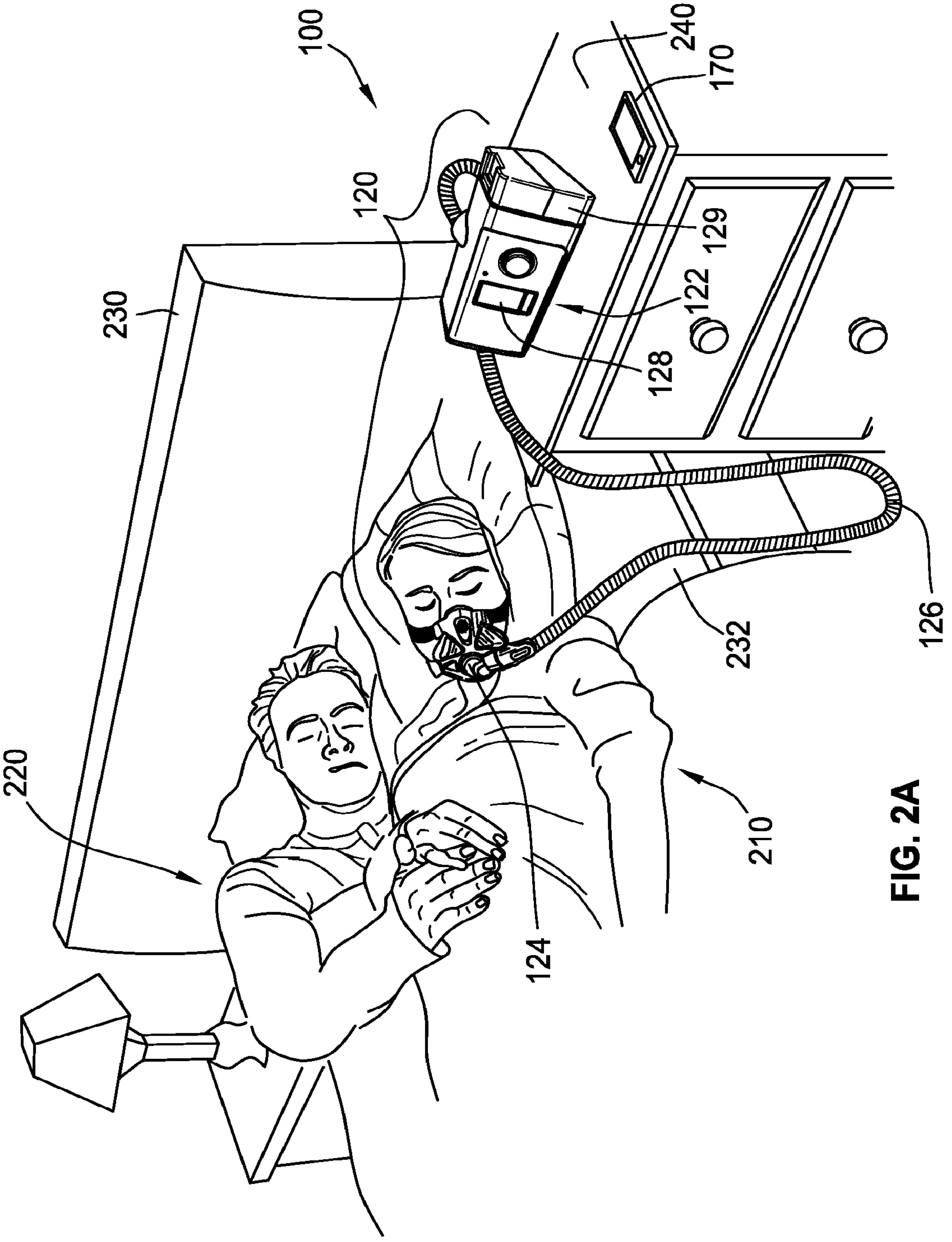
FIG. 2A is a perspective view of a system, a user, and a bed partner, according to certain aspects of the present disclosure.

For example, as shown in FIG. 2A, the respiratory therapy system 100 can be used to treat user 210. The user 210 of the respiratory therapy system 100 and a bed partner 220 are located in a bed 230 and are laying on a mattress 232. The user interface 124 can be worn by the user 210 during a sleep session. The respiratory therapy system 100 generally aids in increasing the air pressure in the throat of the user 210 to aid in preventing the airway from closing and/or narrowing during sleep. The respiratory therapy device 122 can be positioned on a nightstand 240 that is directly adjacent to the bed 232 as shown in FIG. 2, or more generally, on any surface or structure that is generally adjacent to the bed 232 and/or the user 210.

The respiratory therapy device 122 is generally used to generate pressurized air that is delivered to a user (e.g., using one or more motors that drive one or more compressors). In some implementations, the respiratory therapy device 122 generates continuous constant air pressure that is delivered to the user. In other implementations, the respiratory therapy device 122 generates two or more predetermined pressures (e.g., a first predetermined air pressure and a second predetermined air pressure). In still other implementations, the respiratory therapy device 122 is configured to generate a variety of different air pressures within a predetermined range. For example, the respiratory therapy device 122 can deliver at least about 6 cm $H_2O$, at least about 10 cm $H_2O$, at least about 20 cm $H_2O$, between about 6 cm $H_2O$ and about 10 cm $H_2O$, between about 7 cm $H_2O$ and about 12 cm $H_2O$, etc. The respiratory therapy device 122 can also deliver pressurized air at a predetermined flow rate between, for example, about 20 L/min and about 150 L/min, while maintaining a positive pressure (relative to the ambient pressure). The respiratory therapy device 122 includes a housing, a blower motor, an air inlet, and an air outlet. The blower motor is at least partially disposed or integrated within the housing. The blower motor draws air from outside the housing (e.g., atmosphere) via the air inlet and causes pressurized air to flow through the humidifier, and through the air outlet. In some implementations, the air inlet and/or the air outlet include a cover that is moveable between a closed position and an open position (e.g., to prevent or inhibit air from flowing through the air inlet or the air outlet).

The user interface 124 engages a portion of the user's face and delivers pressurized air from the respiratory therapy device 122 to the user's airway to aid in preventing the airway from narrowing and/or collapsing during sleep. This use may also increase the user's oxygen intake during sleep. Depending upon the therapy to be applied, the user interface 124 may form a seal, for example, with a region or portion of the user's face, to facilitate the delivery of gas at a pressure at sufficient variance with ambient pressure to effect therapy, for example, at a positive pressure of about 10 cm $H_2O$ relative to ambient pressure. For other forms of therapy, such as the delivery of oxygen, the user interface may not include a seal sufficient to facilitate delivery to the airways of a supply of gas at a positive pressure of about 10 cm $H_2O$. As shown in FIG. 2A, in some implementations, the user interface 124 is a facial mask that covers the nose and mouth of the user. Alternatively, the user interface 124 can be a nasal mask that provides air to the nose of the user or a nasal pillow mask that delivers air directly to the nostrils of the user. The user interface 124 can include a plurality of straps (e.g., including hook and loop fasteners) for positioning and/or stabilizing the interface on a portion of the user (e.g., the face) and a conformal cushion (e.g., silicone, plastic, foam, etc.) that aids in providing an air-tight seal between the user interface 124 and the user. The user interface 124 can also include one or more vents for permitting the escape of carbon dioxide and other gases exhaled by the user 210. During use, it may be desired to minimize the presence of any unintentional leaks (e.g., leaks around the conformal cushion or other portions of the mask, especially while a user is inhaling), whereas intentional leaks (e.g., venting, such as through included vents, especially while a user is exhaling) may be permitted. In other implementations, the user interface 124 comprises a mouthpiece (e.g., a night guard mouthpiece molded to conform to the user's teeth, a mandibular repositioning device, etc.) for directing pressurized air into the mouth of the user.

The conduit 126 (also referred to as an air circuit or tube) allows the flow of air between two components of a respiratory therapy system 120, such as the respiratory therapy device 122 and the user interface 124. In some implementations, there can be separate limbs of the conduit for inhalation and exhalation. In other implementations, a single limb conduit is used for both inhalation and exhalation.

One or more of the respiratory therapy device 122, the user interface 124, the conduit 126, the display device 128, and the humidifier 129 can contain one or more sensors (e.g., a pressure sensor, a flow rate sensor, or more generally any of the other sensors 130 described herein). These one or more sensors can be use, for example, to measure the air pressure and/or flow rate of pressurized air supplied by the respiratory therapy device 122.

The display device 128 is generally used to display image(s) including still images, video images, or both and/or information regarding the respiratory therapy device 122. For example, the display device 128 can provide information regarding the status of the respiratory therapy device 122 (e.g., whether the respiratory therapy device 122 is on/off, the pressure of the air being delivered by the respiratory therapy device 122, the temperature of the air being delivered by the respiratory therapy device 122, etc.) and/or other information (e.g., a sleep score, the current date/time, personal information for the user 210, etc.). In some implementations, the display device 128 acts as a human-machine interface (HMI) that includes a graphic user interface (GUI) configured to display the image(s) as an input interface. The display device 128 can be an LED display, an OLED display, an LCD display, or the like. The input interface can be, for example, a touchscreen or touch-sensitive substrate, a mouse, a keyboard, or any sensor system configured to sense inputs made by a human user interacting with the respiratory therapy device 122.

The humidifier 129 is coupled to or integrated in the respiratory therapy device 122 and includes a reservoir of water that can be used to humidify the pressurized air delivered from the respiratory therapy device 122. The respiratory therapy device 122 can include a heater to heat the water in the humidifier 129 to generate water vapor. The humidifier 129 can be fluidly coupled to a water vapor inlet of the air pathway between the blower motor and the air outlet, or can be formed in-line with the air pathway between the blower motor and the air outlet. Additionally, in some implementations, the conduit 126 can also include a heating element (e.g., coupled to and/or imbedded in the conduit 126) that heats the pressurized air delivered to the user.

The respiratory therapy system 120 can be used, for example, as a positive airway pressure (PAP) system, a continuous positive airway pressure (CPAP) system, an automatic positive airway pressure system (APAP), a bi-level or variable positive airway pressure system (BPAP or VPAP), a ventilator, or any combination thereof. The CPAP system delivers a predetermined air pressure (e.g., determined by a sleep physician) to the user. The APAP system automatically varies the air pressure delivered to the user based on, for example, respiration data associated with the user. The BPAP or VPAP system is configured to deliver a first predetermined pressure (e.g., an inspiratory positive airway pressure or IPAP) and a second predetermined pressure (e.g., an expiratory positive airway pressure or EPAP) that is lower than the first predetermined pressure.

Referring to FIG. 2A, a portion of the system 100 (FIG. 1), according to some implementations, is illustrated. A user 210 of the respiratory therapy system 120 and a bed partner 220 are located in a bed 230 and are laying on a mattress 232. The user interface 124 (e.g., a full facial mask) can be worn by the user 210 during a sleep session. The user interface 124 is fluidly coupled and/or connected to the respiratory therapy device 122 via the conduit 126. In turn, the respiratory therapy device 122 delivers pressurized air to the user 210 via the conduit 126 and the user interface 124 to increase the air pressure in the throat of the user 210 to aid in preventing the airway from closing and/or narrowing during sleep. The respiratory therapy device 122 can be positioned on a nightstand 240 that is directly adjacent to the bed 230 as shown in FIG. 2A, or more generally, on any surface or structure that is generally adjacent to the bed 230 and/or the user 210.

Referring to back to FIG. 1, the one or more sensors 130 of the system 100 include a pressure sensor 132, a flow rate sensor 134, temperature sensor 136, a motion sensor 138, a microphone 140, a speaker 142, a radio-frequency (RF) receiver 146, a RF transmitter 148, a camera 150, an infrared sensor 152, a photoplethysmogram (PPG) sensor 154, an electrocardiogram (ECG) sensor 156, an electroencephalography (EEG) sensor 158, a capacitive sensor 160, a force sensor 162, a strain gauge sensor 164, an electromyography (EMG) sensor 166, an oxygen sensor 168, an analyte sensor 174, a moisture sensor 176, a Light Detection and Ranging (LiDAR) sensor 178, or any combination thereof. Generally, each of the one or sensors 130 are configured to output sensor data that is received and stored in the memory device 114 or one or more other memory devices.

While the one or more sensors 130 are shown and described as including each of the pressure sensor 132, the flow rate sensor 134, the temperature sensor 136, the motion sensor 138, the microphone 140, the speaker 142, the RF receiver 146, the RF transmitter 148, the camera 150, the infrared sensor 152, the photoplethysmogram (PPG) sensor 154, the electrocardiogram (ECG) sensor 156, the electroencephalography (EEG) sensor 158, the capacitive sensor 160, the force sensor 162, the strain gauge sensor 164, the electromyography (EMG) sensor 166, the oxygen sensor 168, the analyte sensor 174, the moisture sensor 176 more generally, the one or more sensors 130 can include any combination and any number of each of the sensors described and/or shown herein. As described herein, the system 100 generally can be used to generate physiological data associated with a user (e.g., a user of the respiratory therapy system 120) during a sleep session. The physiological data can be analyzed to generate one or more sleep-related parameters, which can include any parameter, measurement, etc. related to the user during the sleep session. The one or more sleep-related parameters that can be determined for the user during the sleep session include, for example, an Apnea-Hypopnea Index (AHI) score, a sleep score, a flow signal, a respiration signal, a respiration rate, an inspiration amplitude, an expiration amplitude, an inspiration-expiration ratio, a number of events per hour, a pattern of events, a stage, pressure settings of the respiratory therapy device 122, a heart rate, a heart rate variability, movement of the user, temperature, EEG activity, EMG activity, arousal, snoring, choking, coughing, whistling, wheezing, or any combination thereof.

The physiological data generated by one or more of the sensors 130 can be used by the control system 110 to determine a sleep-wake signal associated with a user during a sleep session and one or more sleep-related parameters. The sleep-wake signal can be indicative of one or more sleep states, including wakefulness, relaxed wakefulness, micro-awakenings, a rapid eye movement (REM) stage, a first non-REM stage (often referred to as "N1"), a second non-REM stage (often referred to as "N2"), a third non-REM stage (often referred to as "N3"), or any combination thereof.

The sleep-wake signal can also be timestamped to indicate a time that the user enters the bed, a time that the user exits the bed, a time that the user attempts to fall asleep, etc. The sleep-wake signal can be measured by the sensor(s) 130 during the sleep session at a predetermined sampling rate, such as, for example, one sample per second, one sample per 30 seconds, one sample per minute, etc. In some implementations, the sleep-wake signal can also be indicative of a respiration signal, a respiration rate, an inspiration amplitude, an expiration amplitude, an inspiration-expiration ratio, a number of events per hour, a pattern of events, pressure settings of the respiratory therapy device 122, or any combination thereof during the sleep session. The event(s) can include snoring, apneas, central apneas, obstructive apneas, mixed apneas, hypopneas, a mask leak (e.g., from the user interface 124), a restless leg, a sleeping disorder, choking, an increased heart rate, labored breathing, an asthma attack, an epileptic episode, a seizure, or any combination thereof. The one or more sleep-related parameters that can be determined for the user during the sleep session based on the sleep-wake signal include, for example, a total time in bed, a total sleep time, a sleep onset latency, a wake-after-sleep-onset parameter, a sleep efficiency, a fragmentation index, or any combination thereof. In some cases, the physiological data and/or the sleep-related parameters can be analyzed to determine one or more sleep-related scores.

The pressure sensor 132 outputs pressure data that can be stored in the memory device 114 and/or analyzed by the processor 112 of the control system 110. In some implementations, the pressure sensor 132 is an air pressure sensor (e.g., barometric pressure sensor) that generates sensor data indicative of the respiration (e.g., inhaling and/or exhaling) of the user of the respiratory therapy system 120 and/or ambient pressure. In such implementations, the pressure sensor 132 can be coupled to or integrated in the respiratory therapy device 122. The pressure sensor 132 can be, for example, a capacitive sensor, an electromagnetic sensor, a piezoelectric sensor, a strain-gauge sensor, an optical sensor, a potentiometric sensor, or any combination thereof. In some cases, pressure data from the pressure sensor 132 can be used to detect an air leak, such as an unintentional air leak, such as an unintentional air leak between the user interface and the user. In some examples, the pressure sensor 132 can be used to determine a blood pressure of a user.

The flow rate sensor 134 outputs flow rate data that can be stored in the memory device 114 and/or analyzed by the processor 112 of the control system 110. In some implementations, the flow rate sensor 134 is used to determine an air flow rate from the respiratory therapy device 122, an air flow rate through the conduit 126, an air flow rate through the user interface 124, or any combination thereof. In such implementations, the flow rate sensor 134 can be coupled to or integrated in the respiratory therapy device 122, the user interface 124, or the conduit 126. The flow rate sensor 134 can be a mass flow rate sensor such as, for example, a rotary flow meter (e.g., Hall effect flow meters), a turbine flow meter, an orifice flow meter, an ultrasonic flow meter, a hot wire sensor, a vortex sensor, a membrane sensor, or any combination thereof. In some cases, flow rate data from the flow rate sensor 134 can be used to detect an air leak, such as an unintentional air leak, such as an unintentional air leak between the user interface and the user.

The temperature sensor 136 outputs temperature data that can be stored in the memory device 114 and/or analyzed by the processor 112 of the control system 110. In some implementations, the temperature sensor 136 generates temperatures data indicative of a core body temperature of the user 210 (FIG. 2A), a skin temperature of the user 210, a temperature of the air flowing from the respiratory therapy device 122 and/or through the conduit 126, a temperature in the user interface 124, an ambient temperature, or any combination thereof. The temperature sensor 136 can be, for example, a thermocouple sensor, a thermistor sensor, a silicon band gap temperature sensor or semiconductor-based sensor, a resistance temperature detector, or any combination thereof. In some cases, the temperature sensor 136 can be a thermal imaging device, such as a thermal imaging camera. In an example, a thermal imaging device (e.g., coupled to an external device 170, such as a smartphone) can be used to generate temperature data, which can be used to identify temperature changes on the user's skin, which may be indicative of an unintentional air leak.

The motion sensor 138 outputs motion data that can be stored in the memory device 114 and/or analyzed by the processor 112 of the control system 110. The motion sensor 138 can be used to detect movement of the user during the sleep session, and/or detect movement of any of the components of the respiratory therapy system 120, such as the respiratory therapy device 122, the user interface 124, or the conduit 126. The motion sensor 138 can include one or more inertial sensors, such as accelerometers, gyroscopes, and magnetometers. In some implementations, the motion sensor 138 alternatively or additionally generates one or more signals representing bodily movement of the user, from which may be obtained a signal representing a sleep state of the user; for example, via a respiratory movement of the user. In some implementations, the motion data from the motion sensor 138 can be used in conjunction with additional data from another one of the sensors 130 to determine the sleep state of the user.

The microphone 140 outputs sound data (e.g., acoustic data) that can be stored in the memory device 114 and/or analyzed by the processor 112 of the control system 110. The microphone 140 can be used to record sound(s) during a sleep session (e.g., sounds from the user 210) to determine (e.g., using the control system 110) one or more sleep-related parameters, as described in further detail herein. The microphone 140 can be coupled to or integrated in the respiratory therapy device 122, the use interface 124, the conduit 126, or the external device 170. In some cases, the microphone 140 can be used to obtain acoustic data, which can be used to help identify an unintentional air leak, as disclosed herein. For example, a microphone 140 (e.g., coupled to an external device 170, such as a smartphone) can be maneuvered in a known path adjacent a user interface worn by a user while collecting acoustic data, which can be analyzed to identify a location of an unintentional air leak at the user interface. In some implementations, the system 100 includes a plurality of microphones (e.g., two or more microphones and/or an array of microphones with beamforming) such that sound data generated by each of the plurality of microphones can be used to discriminate the sound data generated by another of the plurality of microphones.

The speaker 142 outputs sound waves that are audible to a user of the system 100 (e.g., the user 210 of FIG. 2A), although that need not always be the case. The speaker 142 can be used, for example, as an alarm clock or to play an alert or message to the user 210 (e.g., in response to an event). The speaker 142 can be coupled to or integrated in the respiratory therapy device 122, the user interface 124, the conduit 126, or the external device 170. In some cases, the speaker 142 can output infrasonic and/or ultrasonic sound waves.

The microphone 140 and the speaker 142 can be used as separate devices. In some implementations, the microphone 140 and the speaker 142 can be combined into an acoustic sensor 141, as described in, for example, WO 2018/050913 and WO 2020/104465, each of which is hereby incorporated by reference herein in its entirety. In such implementations, the speaker 142 generates or emits sound waves at a predetermined interval and the microphone 140 detects the reflections of the emitted sound waves from the speaker 142. The sound waves generated or emitted by the speaker 142 have a frequency that is not audible to the human ear (e.g., below 20 Hz or above around 18 kHz) so as not to disturb the sleep of the user 210 or the bed partner 220 (FIG. 2A). Based at least in part on the data from the microphone 140 and/or the speaker 142, the control system 110 can determine a location of the user 210 (FIG. 2A), a location of a user interface 124, a location of an unintentional air leak, and/or one or more of the sleep-related parameters described herein, such as, for example, a respiration signal, a respiration rate, an inspiration amplitude, an expiration amplitude, an inspiration-expiration ratio, a number of events per hour, a pattern of events, a sleep state, a sleep stage, pressure settings of the respiratory therapy device 122, or any combination thereof. In such a context, a sonar sensor may be understood to concern an active acoustic sensing, such as by generating and/or transmitting ultrasound and/or low frequency ultrasound sensing signals (e.g., in a frequency range of about 17-23 kHz, 18-22 kHz, or 17-18 kHz, for example), through the air.

The RF transmitter 148 generates and/or emits radio waves having a predetermined frequency and/or a predetermined amplitude (e.g., within a high frequency band, within a low frequency band, long wave signals, short wave signals, etc.). The RF receiver 146 detects the reflections of the radio waves emitted from the RF transmitter 148, and this data can be analyzed by the control system 110 to determine a location of the user 210 (FIG. 2A), a location of a user interface 124, a location of an unintentional air leak, and/or one or more of the sleep-related parameters described herein. An RF receiver (either the RF receiver 146 and the RF transmitter 148 or another RF pair) can also be used for wireless communication between the control system 110, the respiratory therapy device 122, the one or more sensors 130, the external device 170, or any combination thereof. While the RF receiver 146 and RF transmitter 148 are shown as being separate and distinct elements in FIG. 1, in some implementations, the RF receiver 146 and RF transmitter 148 are combined as a part of an RF sensor 147. In some such implementations, the RF sensor 147 includes a control circuit. The specific format of the RF communication could be Wi-Fi, Bluetooth, etc.

In some implementations, the RF sensor 147 is a part of a mesh system. One example of a mesh system is a Wi-Fi mesh system, which can include mesh nodes, mesh router(s), and mesh gateway(s), each of which can be mobile/movable or fixed. In such implementations, the Wi-Fi mesh system includes a Wi-Fi router and/or a Wi-Fi controller and one or more satellites (e.g., access points), each of which include an RF sensor that the is the same as, or similar to, the RF sensor 147. The Wi-Fi router and satellites continuously communicate with one another using Wi-Fi signals. The Wi-Fi mesh system can be used to generate motion data based on changes in the Wi-Fi signals (e.g., differences in received signal strength) between the router and the satellite(s) due to an object or person moving partially obstructing the signals. The motion data can be indicative of motion, breathing, heart rate, gait, falls, behavior, etc., or any combination thereof.

The camera 150 outputs image data reproducible as one or more images (e.g., still images, video images, thermal images, or any combination thereof) that can be stored in the memory device 114. The image data from the camera 150 can be used by the control system 110 to determine one or more of the sleep-related parameters described herein, such as, for example, one or more events (e.g., periodic limb movement or restless leg syndrome), a respiration signal, a respiration rate, an inspiration amplitude, an expiration amplitude, an inspiration-expiration ratio, a number of events per hour, a pattern of events, a sleep state, a sleep stage, or any combination thereof. Further, the image data from the camera 150 can be used to, for example, identify a location of the user, to determine chest movement of the user, to determine air flow of the mouth and/or nose of the user, to determine a time when the user 210 enters the bed 230 (FIG. 2A), and to determine a time when the user 210 exits the bed 230. In some cases, a camera 150 can be used to capture an encoded image (e.g., a barcode, such as a 2D barcode or a Quick Response (QR) code), which can be decoded and used by the control system 110. For example, a camera 150 can be directed towards a user interface 124 having an encoded image thereon (e.g., a QR code sticker or imprint), in which case the control system 110 can decode the encoded image to obtain identification information associated with the user interface 124. In some cases, image data can be presented on a display device 172. In an example, a camera 150 can be directed towards a user wearing a user interface 124, in which case the resultant image data can be presented, live or delayed, using the display device 172. In some cases, further information (e.g., augmented reality (AR) information) can be superimposed on the images, such as to annotate regions of interest (e.g., unintentional air leaks) in the image or provide instructions or information. The camera 150 can operate in the visible spectrum, although that need not always be the case. In some cases, for example, a camera 150 can be a thermal camera, which can operate as a temperature sensor 136.

The infrared (IR) sensor 152 outputs infrared image data reproducible as one or more infrared images (e.g., still images, video images, or both) that can be stored in the memory device 114. The infrared data from the IR sensor 152 can be used to determine one or more sleep-related parameters during a sleep session, including a temperature of the user 210 and/or movement of the user 210. The IR sensor 152 can also be used in conjunction with the camera 150 when measuring the presence, location, and/or movement of the user 210. The IR sensor 152 can detect infrared light having a wavelength between about 700 nm and about 1 mm, for example, while the camera 150 can detect visible light having a wavelength between about 380 nm and about 740 nm, although that need not always be the case.

The PPG sensor 154 outputs physiological data associated with the user 210 (FIG. 2A) that can be used to determine one or more sleep-related parameters, such as, for example, a heart rate, a heart rate variability, a cardiac cycle, respiration rate, an inspiration amplitude, an expiration amplitude, an inspiration-expiration ratio, estimated blood pressure parameter(s), or any combination thereof. The PPG sensor 154 can be worn by the user 210, embedded in clothing and/or fabric that is worn by the user 210, embedded in and/or coupled to the user interface 124 and/or its associated headgear (e.g., straps, etc.), etc.

The ECG sensor 156 outputs physiological data associated with electrical activity of the heart of the user 210. In some implementations, the ECG sensor 156 includes one or more electrodes that are positioned on or around a portion of the user 210 during the sleep session. The physiological data from the ECG sensor 156 can be used, for example, to determine one or more of the sleep-related parameters described herein.

The EEG sensor 158 outputs physiological data associated with electrical activity of the brain of the user 210. In some implementations, the EEG sensor 158 includes one or more electrodes that are positioned on or around the scalp of the user 210 during the sleep session. The physiological data from the EEG sensor 158 can be used, for example, to determine a sleep state of the user 210 at any given time during the sleep session. In some implementations, the EEG sensor 158 can be integrated in the user interface 124 and/or the associated headgear (e.g., straps, etc.).

The capacitive sensor 160, the force sensor 162, and the strain gauge sensor 164 output data that can be stored in the memory device 114 and used by the control system 110 to determine one or more of the sleep-related parameters described herein. The EMG sensor 166 outputs physiological data associated with electrical activity produced by one or more muscles. The oxygen sensor 168 outputs oxygen data indicative of an oxygen concentration of gas (e.g., in the conduit 126 or at the user interface 124). The oxygen sensor 168 can be, for example, an ultrasonic oxygen sensor, an electrical oxygen sensor, a chemical oxygen sensor, an optical oxygen sensor, or any combination thereof. In some cases, oxygen data can be indicative of an unintentional air leak. In some implementations, the one or more sensors 130 also include a galvanic skin response (GSR) sensor, a blood flow sensor, a respiration sensor, a pulse sensor, a sphygmomanometer sensor, an oximetry sensor, or any combination thereof.

The analyte sensor 174 can be used to detect the presence of an analyte in the exhaled breath of the user 210. The data output by the analyte sensor 174 can be stored in the memory device 114 and used by the control system 110 to determine the identity and concentration of any analytes in the breath of the user 210. In some implementations, the analyte sensor 174 is positioned near a mouth of the user 210 to detect analytes in breath exhaled from the user 210's mouth. For example, when the user interface 124 is a facial mask that covers the nose and mouth of the user 210, the analyte sensor 174 can be positioned within the facial mask to monitor the user 210's mouth breathing. In other implementations, such as when the user interface 124 is a nasal mask or a nasal pillow mask, the analyte sensor 174 can be positioned near the nose of the user 210 to detect analytes in breath exhaled through the user's nose. In still other implementations, the analyte sensor 174 can be positioned near the user 210's mouth when the user interface 124 is a nasal mask or a nasal pillow mask. In this implementation, the analyte sensor 174 can be used to detect whether any air is inadvertently leaking from the user 210's mouth. In some implementations, the analyte sensor 174 is a volatile organic compound (VOC) sensor that can be used to detect carbon-based chemicals or compounds. In some implementations, the analyte sensor 174 can also be used to detect whether the user 210 is breathing through their nose or mouth. For example, if the data output by an analyte sensor 174 positioned near the mouth of the user 210 or within the facial mask (in implementations where the user interface 124 is a facial mask) detects the presence of an analyte, the control system 110 can use this data as an indication that the user 210 is breathing through their mouth. In some cases, one or more analyte sensors 174 positioned around a user interface 124 (e.g., around an outer edge of the user interface 124) can be used to detect the presence of analyte around an edge of the user interface 124. In such cases, presence of the analyte in a region may be indicative of an unintentional air leak near that region.

The moisture sensor 176 outputs data that can be stored in the memory device 114 and used by the control system 110. The moisture sensor 176 can be used to detect moisture in various areas surrounding the user (e.g., inside the conduit 126 or the user interface 124, near the user 210's face, near the connection between the conduit 126 and the user interface 124, near the connection between the conduit 126 and the respiratory therapy device 122, etc.). Thus, in some implementations, the moisture sensor 176 can be coupled to or integrated in the user interface 124 or in the conduit 126 to monitor the humidity of the pressurized air from the respiratory therapy device 122. In other implementations, the moisture sensor 176 is placed near any area where moisture levels need to be monitored. The moisture sensor 176 can also be used to monitor the humidity of the ambient environment surrounding the user 210, for example, the air inside the bedroom. In some cases, one or more moisture sensors 176 positioned around a user interface 124 (e.g., around an outer edge of the user interface 124) can be used to detect the presence of moisture around an edge of the user interface 124. In such cases, presence of moisture in a region may be indicative of an unintentional air leak near that region.

One or more Light Detection and Ranging (LiDAR) sensors 178 can be used for depth sensing. This type of optical sensor (e.g., laser sensor) can be used to detect objects and build three dimensional (3D) maps of the surroundings, such as of a living space. In some cases, LiDAR can be used to generate a 3D map of the user, the user wearing a user interface 124, and/or the user interface 124 itself. LiDAR can generally utilize a pulsed laser to make time of flight measurements. LiDAR is also referred to as 3D laser scanning. In an example of use of such a sensor, a fixed or mobile device (such as a smartphone) having a LiDAR sensor 178 can measure and map an area extending 5 meters or more away from the sensor. The LiDAR data can be fused with point cloud data estimated by an electromagnetic RADAR sensor, for example. The LiDAR sensor(s) 178 may also use artificial intelligence (AI) to automatically geofence RADAR systems by detecting and classifying features in a space that might cause issues for RADAR systems, such a glass windows (which can be highly reflective to RADAR). LiDAR can also be used to provide an estimate of the height of a person, as well as changes in height when the person sits down, or falls down, for example. LiDAR may be used to form a 3D mesh representation of an environment. In a further use, for solid surfaces through which radio waves pass (e.g., radio-translucent materials), the LiDAR may reflect off such surfaces, thus allowing a classification of different type of obstacles.

In some implementations, the one or more sensors 130 also includes a galvanic skin response (GSR) sensor, a blood flow sensor, a respiration sensor, a pulse sensor, a sphygmomanometer sensor, an oximetry sensor, a sonar sensor, a RADAR sensor, a blood glucose sensor, a color sensor, a pH sensor, an air quality sensor, a tilt sensor, a rain sensor, a soil moisture sensor, a water flow sensor, an alcohol sensor, or any combination thereof.

While shown separately in FIG. 1, any combination of the one or more sensors 130 can be integrated in and/or coupled to any one or more of the components of the system 100, including the respiratory therapy device 122, the user interface 124, the conduit 126, the humidifier 129, the control system 110, the external device 170, or any combination thereof. For example, the acoustic sensor 141 and/or the camera 150 can be integrated in and/or coupled to the external device 170. In such implementations, the external device 170 can be considered a secondary device that generates additional or secondary data for use by the system 100 (e.g., the control system 110) according to some aspects of the present disclosure. In some implementations, at least one of the one or more sensors 130 is not coupled to the respiratory therapy device 122, the control system 110, or the external device 170, and is positioned generally adjacent to the user 210 during the sleep session (e.g., positioned on or in contact with a portion of the user 210, worn by the user 210, coupled to or positioned on the nightstand, coupled to the mattress, coupled to the ceiling, etc.).

One or more of the respiratory therapy device 122, the user interface 124, the conduit 126, the display device 128, and the humidifier 129 can contain one or more sensors (e.g., a pressure sensor, a flow rate sensor, or more generally any of the other sensors 130 described herein). These one or more sensors can be used, for example, to measure the air pressure and/or flow rate of pressurized air supplied by the respiratory therapy device 122.

The data from the one or more sensors 130 can be analyzed to determine one or more sleep-related parameters, which can include a respiration signal, a respiration rate, a respiration pattern, an inspiration amplitude, an expiration amplitude, an inspiration-expiration ratio, an occurrence of one or more events, a number of events per hour, a pattern of events, a sleep state, an apnea-hypopnea index (AHI), or any combination thereof. The one or more events can include snoring, apneas, central apneas, obstructive apneas, mixed apneas, hypopneas, a mask leak, a cough, a restless leg, a sleeping disorder, choking, an increased heart rate, labored breathing, an asthma attack, an epileptic episode, a seizure, increased blood pressure, or any combination thereof. Many of these sleep-related parameters are physiological parameters, although some of the sleep-related parameters can be considered to be non-physiological parameters. Other types of physiological and non-physiological parameters can also be determined, either from the data from the one or more sensors 130, or from other types of data.

The external device 170 (FIG. 1) includes a display device 172. The external device 170 can be, for example, a mobile device such as a smartphone, a tablet, a gaming console, a smart watch, a laptop, or the like. Alternatively, the external device 170 can be an external sensing system, a television (e.g., a smart television) or another smart home device (e.g., a smart speaker(s) such as Google Home, Amazon Echo, Alexa etc.). In some implementations, the user device is a wearable device (e.g., a smart watch). The display device 172 is generally used to display image(s) including still images, video images, or both. In some implementations, the display device 172 acts as a human-machine interface (HMI) that includes a graphic user interface (GUI) configured to display the image(s) and an input interface. The display device 172 can be an LED display, an OLED display, an LCD display, or the like. The input interface can be, for example, a touchscreen or touch-sensitive substrate, a mouse, a keyboard, or any sensor system configured to sense inputs made by a human user interacting with the external device 170. In some implementations, one or more user devices can be used by and/or included in the system 100.

While the control system 110 and the memory device 114 are described and shown in FIG. 1 as being a separate and distinct component of the system 100, in some implementations, the control system 110 and/or the memory device 114 are integrated in the external device 170 and/or the respiratory therapy device 122. Alternatively, in some implementations, the control system 110 or a portion thereof (e.g., the processor 112) can be located in a cloud (e.g., integrated in a server, integrated in an Internet of Things (IoT) device, connected to the cloud, be subject to edge cloud processing, etc.), located in one or more servers (e.g., remote servers, local servers, etc., or any combination thereof.

While system 100 is shown as including all of the components described above, more or fewer components can be included in a system for generating physiological data and determining a recommended notification or action for the user according to implementations of the present disclosure. For example, a first alternative system includes the control system 110, the memory device 114, and at least one of the one or more sensors 130. As another example, a second alternative system includes the control system 110, the memory device 114, at least one of the one or more sensors 130, and the external device 170. As yet another example, a third alternative system includes the control system 110, the memory device 114, the respiratory therapy system 120, at least one of the one or more sensors 130, and the external device 170. Thus, various systems can be formed using any portion or portions of the components shown and described herein and/or in combination with one or more other components.

Figure 2B:
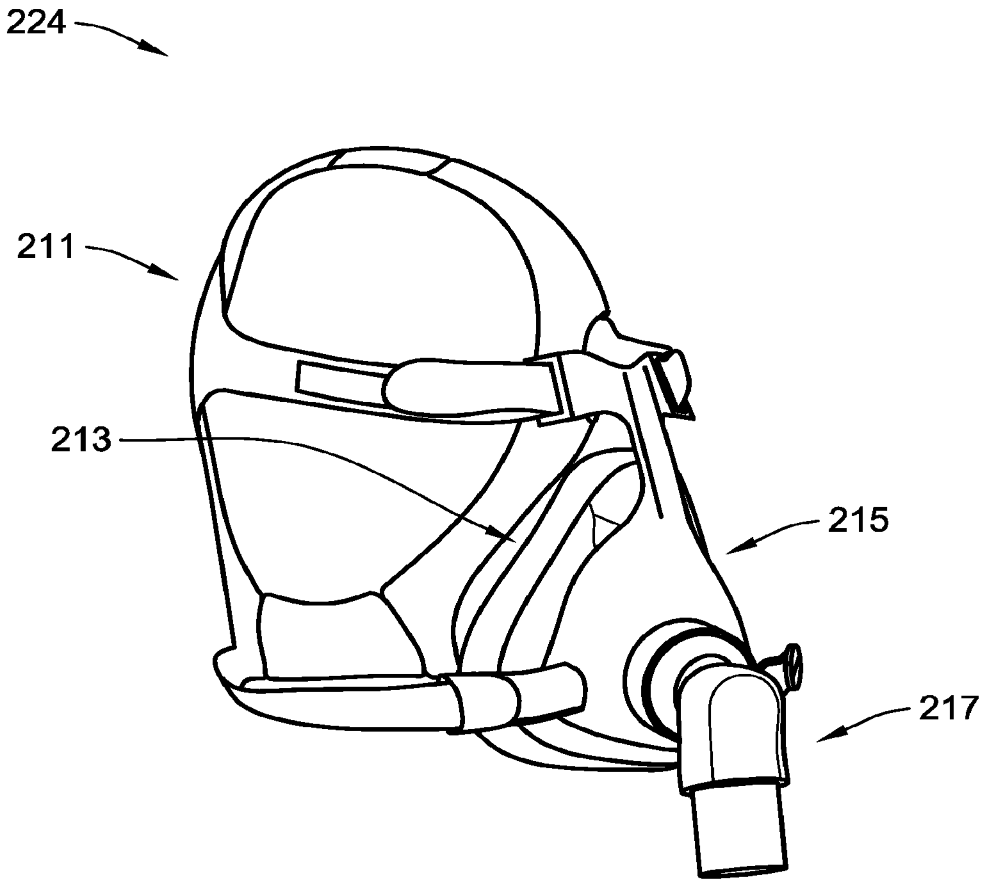
FIG. 2B is an axonometric view of a user interface, according to certain aspects of the present disclosure.

FIG. 2B is an axonometric view of a user interface 224, according to certain aspects of the present disclosure. User interface 224 may be the same as or similar to user interface 124 as discussed herein with respect to FIGS. 1 and 2A, and can be used in conjunction with any of the above-described components or features of system 100, including respiratory therapy system 120 and respiratory therapy device 122. The user interface 124 includes a strap assembly 211, a cushion 213, a frame 215, and a connector 217. The strap assembly 211 is configured to be positioned generally about at least a portion of the user's head when the user wears the user interface 224. The strap assembly 211 can be coupled to the frame 215 and positioned on the user's head such that the user's head is positioned between the strap assembly 211 and the frame 215.

The cushion 213 and the frame 2define a volume of space around the mouth and/or nose of the user. When the respiratory therapy system is in use, this volume of space receives pressurized air (e.g., from the respiratory therapy device via the conduit) for passage into the airway(s) of the user. The headgear (e.g., strap assembly 211) is generally used to aid in positioning and/or stabilizing the user interface 224 on a portion of the user (e.g., the face), and along with the cushion 213 (which, for example, can comprise silicone, plastic, foam, etc.) aids in providing a substantially air-tight seal between the user interface 224 and the user. In some implementations the headgear includes one or more straps (e.g., including hook and loop fasteners). The connector 217 is generally used to couple (e.g., connect and fluidly couple) the conduit to the cushion 213 and/or frame 215. Alternatively, the conduit can be directly coupled to the cushion 213 and/or frame 215 without the connector 217. The user interface 224 can also include one or more vents for permitting the escape of carbon dioxide and other gases exhaled by the user.

In some implementations, the cushion 213 is positioned between the user's face and the frame 215 to form a seal on the user's face. The conduit can be coupled to the air outlet of a respiratory therapy device (such as respiratory therapy device 122). A blower motor in the respiratory therapy device is operable to flow pressurized air out of the air outlet, to thereby provide pressurized air to the user. The pressurized air can flow from the respiratory therapy device and through the conduit, the connector 217, the frame 215, and the cushion 213, until the air reaches the user's airway through the user's mouth, nose, or both.

Figure 3:
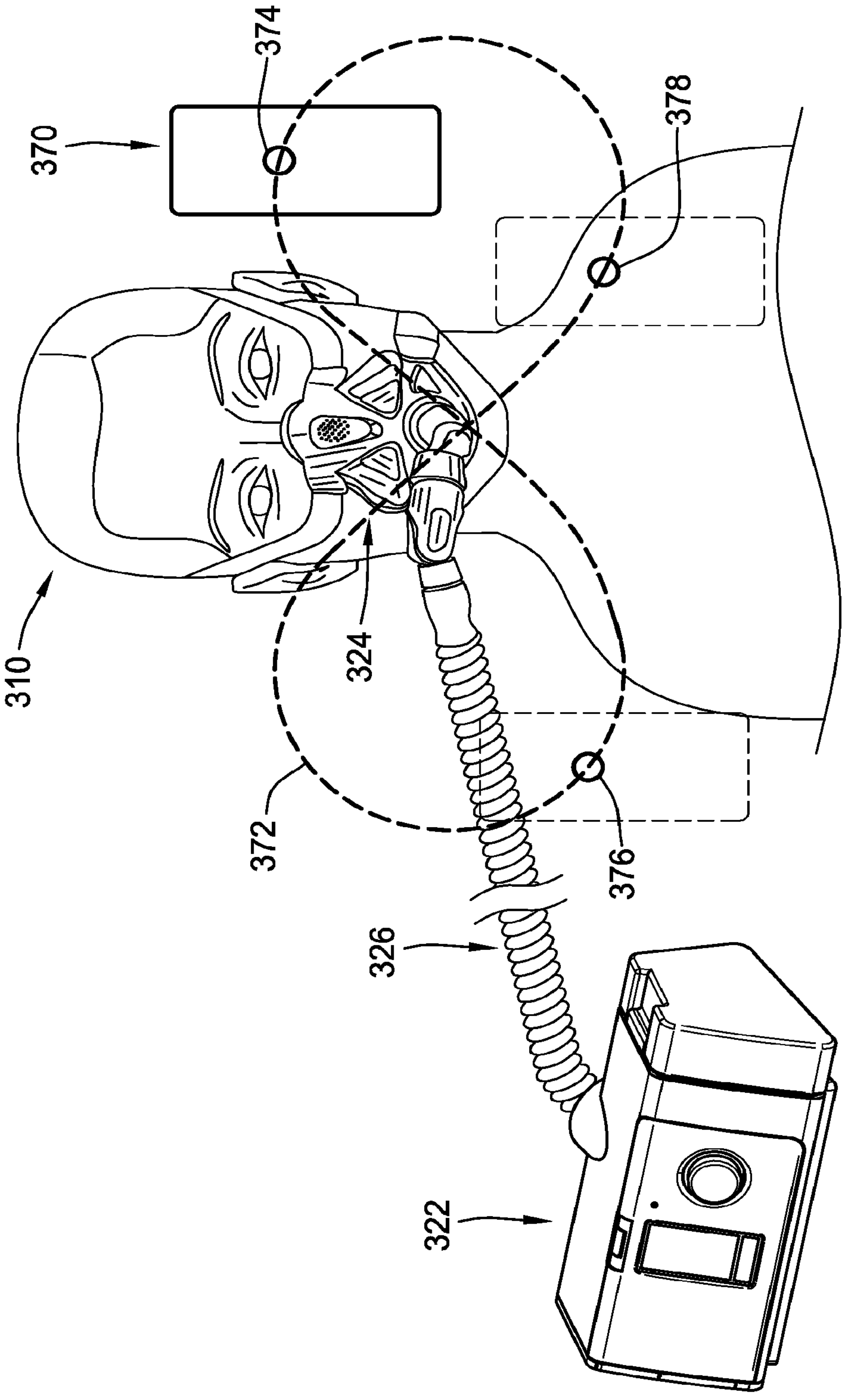
FIG. 3 is a front view of a user wearing a user interface and interacting with a computing device, according to certain aspects of the present disclosure.
Figure 4:
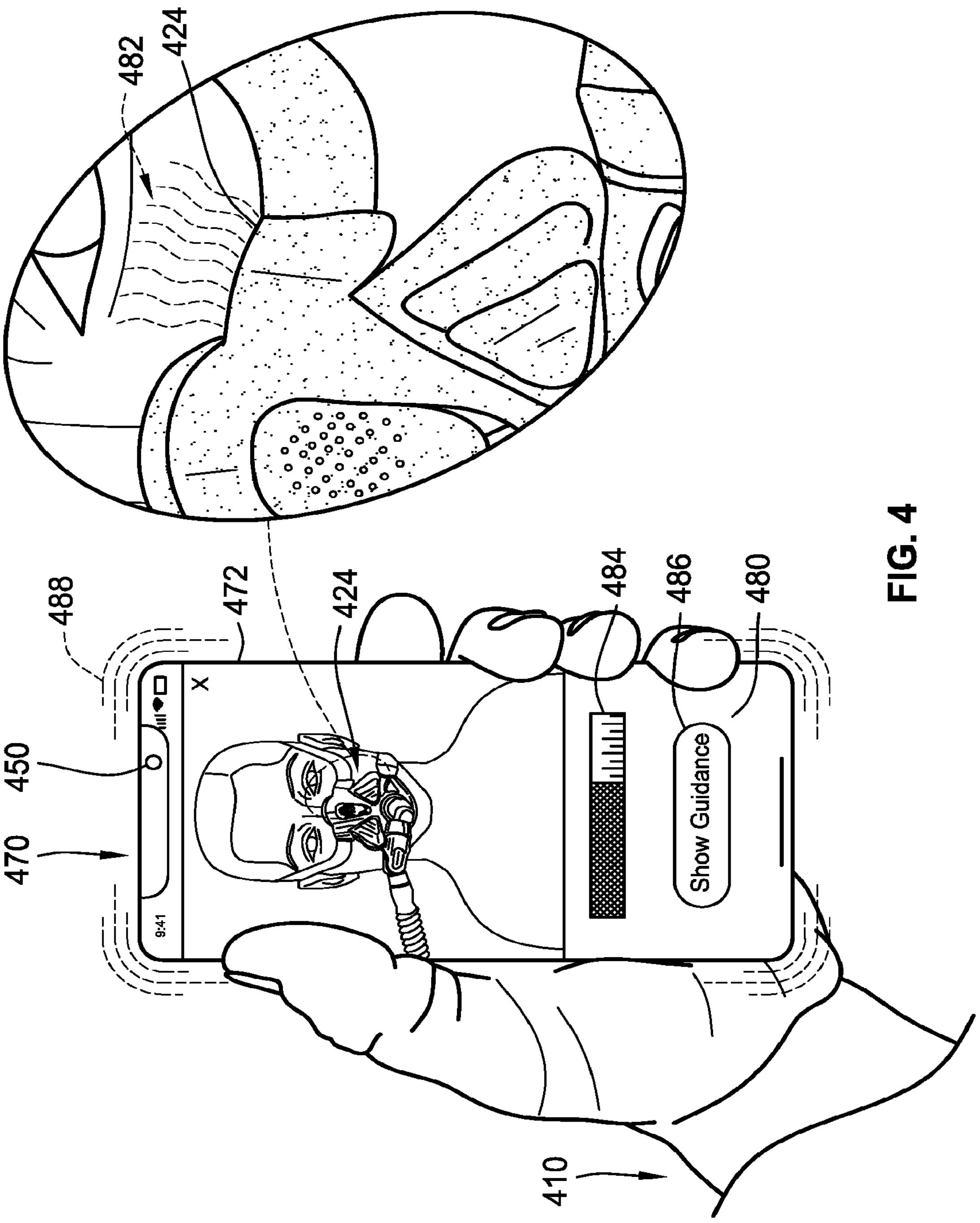
FIG. 4 is a user's view of a computing device being used to identify a leak in the user interface, according to certain aspects of the present disclosure.
Figure 5:
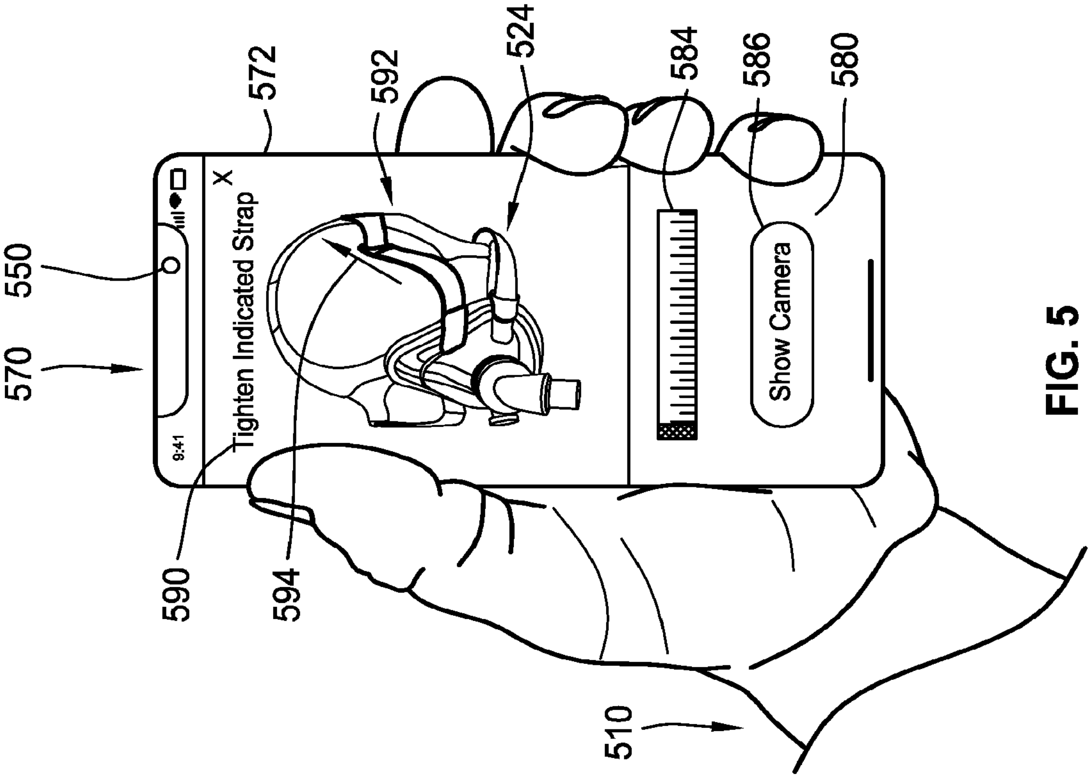
FIG. 5 is a user's view of a computing device depicting fitting guidance, according to certain aspects of the present disclosure.

FIG. 3 is a front view of a user 310 wearing a user interface 324 and interacting with a computing device 370, according to certain aspects of the present disclosure. User 310 can be user 210 of FIG. 2A, such as before falling asleep or after waking. User interface 324 can be a user interface of a system, such as user interface 124 of system 100. A conduit 326 can couple the user interface 324 to a respiratory therapy device. The computing device 370 can be an external device (e.g., external device 170 of FIG. 1). As depicted in FIG. 3, computing device 370 can be a smartphone, although any other suitable computing device can be used. FIGS. 3-5 described certain aspects and features of the present disclosure with reference to a computing device for illustrative purposes, however the various features and aspects of the present disclosure performed by such a computing device may be performed by other elements of the system (e.g., system 100 of FIG. 1), as appropriate.

User 310 can engage an app or other process to perform air leak detection using the computing device 370. As part of the air leak detection process, the user 310 can be directed to maneuver the computing device 370 through different positions (e.g., position A 374, position B 376, and position C 378) while the computing device 370 takes measurements using one or more sensors (e.g., one or more sensors 130 of FIG. 1). For illustrative purposes, the arms/hands of user 310 are not shown in FIG. 3, although user 310 (or another person such as a nurse, or caregiver, etc.) may be holding the computing device 370 during use.

Figure 8:
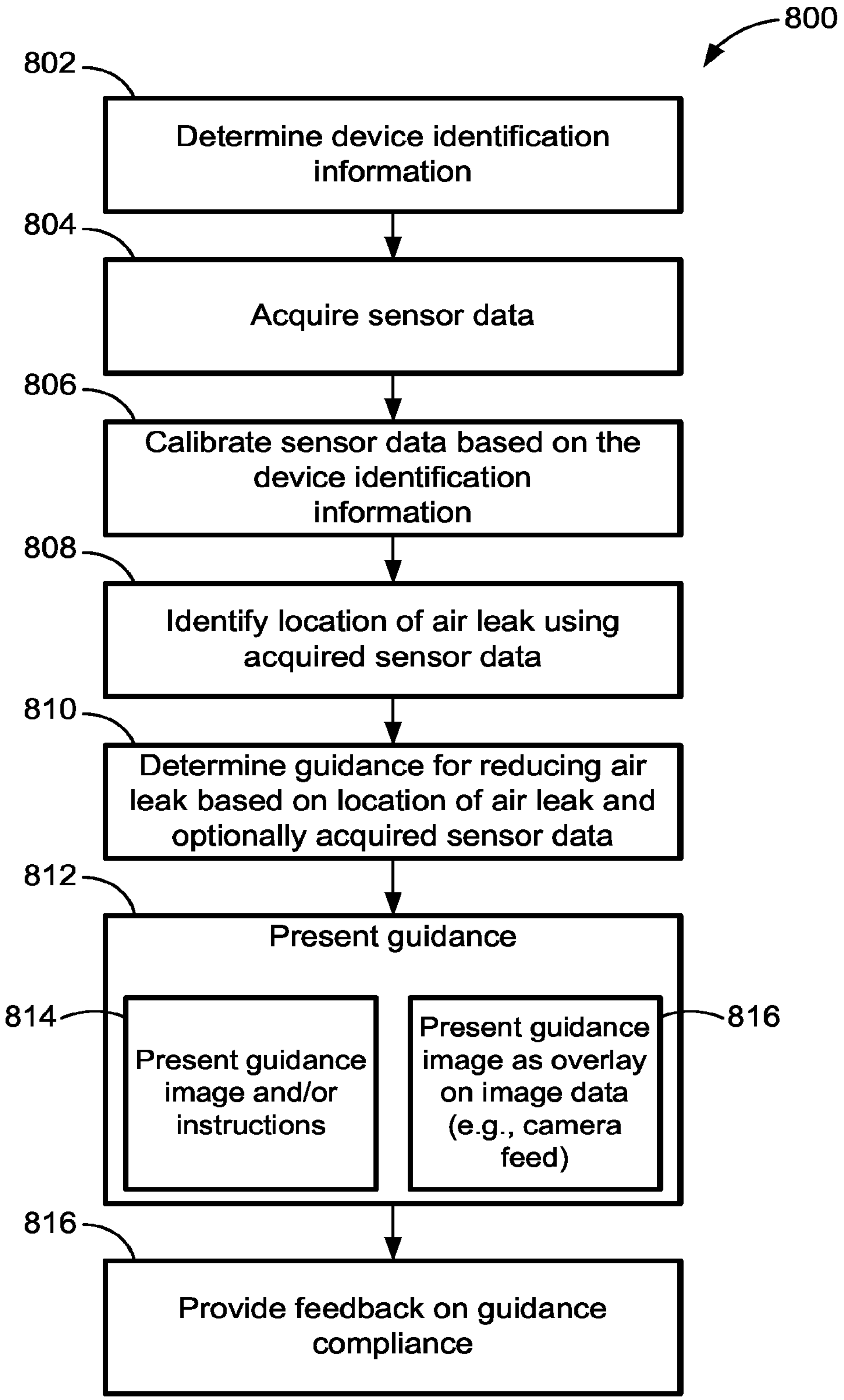
FIG. 8 is a flowchart depicting a process for calibrating sensor data for identifying a leak in a user interface and presenting guidance, according to certain aspects of the present disclosure.

In some cases, the user 310 can be directed to maneuver the computing device 370 along or approximately along a preset path 372, such as a FIG. 8 path (e.g., a horizontal and/or a vertical FIG. 8 path) or other known path (e.g., a circular path). In some cases, the path is a smooth path (e.g., without sharp angles). In some cases, the path 372 is designed to allow the one or more sensors of the computing device 370 to capture sensor data at certain positions relative to the user interface 324. For the purpose of describing FIG. 3, the terms left, right, up, and down can refer to left, right, up, and down directions from a centerline of the user interface 324 extending out of the page of FIG. 3. For example, the right and left sides of the user interface 324 can be the left and right sides of the image of FIG. 3, respectively, and the top and bottom sides of the user interface 324 can be the top and bottom sides of the image of FIG. 3, respectively. In some cases, the path 372 can be established to move the one or more sensors (e.g., computing device 370 containing or otherwise supporting the one or more sensors) so that sensor data can be acquired from different sides of the user interface 324. For example, path 372 can move so sensor data can be acquired from a position left of the user interface 324 (e.g., position A 374 or position C 375), a position right of the user interface 324 (e.g., position B 376), a position above the user interface 324 (e.g., position A 374), and/or a position below the user interface 324 (e.g., position B 376 or position C 378).

Thus, as disclosed herein, sensor data acquired at different positions can be used to triangulate or otherwise identify a location of a potential air leak (e.g., a potential unintentional air leak). In some cases, sensor data can be acquired from at least two different positions, at least three different positions, at least four different positions, or more than four positions, although this need not always be the case.

In some cases, a display of the computing device 370 can provide dynamic and/or real-time feedback to the user 310 to ensure the user 310 is maneuvering the computing device 370 along path 372. For example, motion data capture by one or more sensors (e.g., motion sensor 138 and/or camera 150) can be used to estimate a position of the computing device 370 relative the user interface 324. This estimated position can be used to determine whether or not the user 310 is maneuvering the computing device 370 along the path 372 and/or can be used to provide feedback to facilitate the user 310 maneuvering the computing device 370 along the path 372.

In some cases, computing device 370 can be communicatively coupled to the respiratory therapy device 322 (e.g., via a wireless data link), such as to send or receive data. For example, the computing device 370 can send a flow rate command to the respiratory therapy device 322 to alter the flow rate of the respiratory therapy device 322. The flow rate command can cause the respiratory therapy device 322 to operate at a particular flow rate and/or at a particular sequence of flow rates. In another example, the computing device 370 can receive sensor data from one or more sensors of the respiratory therapy device 322, which can be used to supplement sensor data collected by the one or more sensors of the computing device 370.

FIG. 4 is a user's view of a computing device being used to identify a leak in the user interface 424, according to certain aspects of the present disclosure. Computing device 470 can be computing device 370 of FIG. 3. The view in FIG. 4 can be the view from user 310 of FIG. 3 as looking at computing device 370 of FIG. 3.

The computing device 370 can include a camera 450 (e.g., a user-facing camera), a display device 472 (e.g., a user-facing display), and optionally any number of additional sensors (e.g., motion sensors, IR sensors, and the like). The computing device 370 can include one or more audio sensors, such as one or more microphones. The one or more microphones can be located in any suitable location, such as along a bottom edge of the computing device 370, near an earpiece of the computing device 370, or on a rear side of the computing device 370.

As the user 410 maneuvers the computing device 470 with respect to the user interface 424, computing device 470 can collect image data from the camera 450. While depicted with a user-facing camera and user-facing display device in FIG. 4, that need not always be the case. Image data from the camera 450 can be presented as part of a display 480 (e.g., a graphical user interface). The display 480 can include live or delayed image data, such as a live image of the user 410 holding the computing device 470.

As the user 410 maneuvers the computing device 470 with respect to the user interface 424 (e.g., along path 372 of FIG. 3), the computing device 470 can process sensor data to identify a location of an air leak (e.g., an unintentional air leak). The location of the air leak can be identified as a specific or relative location in a three-dimensional model (e.g., a three-dimensional mapping of the user interface 424 being worn by user 410), a specific or relative location in a two-dimensional plane (e.g., on a two-dimensional representation of the user interface 424 being worn by user 410), or a specific or relative distance away from the computing device 470.

The computing device 470 can provide feedback to the user indicative of the location (e.g., a specific location or relative location) of the air leak. Any suitable feedback can be provided, including visual, audio, and/or haptic feedback. Visual feedback can be provided by the display device 472, another visual element of the computing device 470 (e.g., a light emitting diode), or a visual element of another device. Audio feedback can be provided by the computing device 470 (e.g., via a speaker of the computing device 470) or an audio element of another device. Haptic feedback can be provided by the computing device (e.g., via a vibration motor or haptic feedback device of the computing device 470) or a haptic feedback element of another device. Any combination of different types of feedback can be used to indicate a specific or relative location of the air leak, as well as the presence or absence of an air leak.

In some cases, the computing device 470 can provide annotations on the display 480, such as overlaid on image data (e.g., a live video or image or the user 410) or presented elsewhere on the display 480. These annotations can indicate or call attention to an air leak. In some cases, the location of where the annotation is presented can be based on the location of the air leak. For example, a 3D or 2D location of an air leak can be used to present an air leak annotation 482 that is overlaid on image data. As depicted in the zoomed-in portion of FIG. 4, an air leak around the edge of the user interface 424 is highlighted through the use of an air leak annotation 482. Air leak annotation 482 is depicted as lines radiating from the point of the air leak, can may be present in a fashion designed to call attention to the location, such as through the use of inverted colors, bright colors, flashing or moving elements, or other such elements. In some cases, an intensity of the air leak annotation 482 (e.g., a size of the annotation, color of the annotation, flashing rate or movement rate of the annotation, or the like) can be used to indicate an intensity of the air leak itself. The air leak annotation 482 can facilitate easy and quick identification of the location and/or extent of the air leak, even in cases where the air leak may not be visible to and/or felt by the user 410.

In another example, an intensity of the air leak can be presented on display 480 as an air leak meter 484, which can be a different type of annotation. The air leak meter 484 can present an actual or relative intensity of the air leak as determined by the one or more sensors. The air leak meter 484 can update in real-time to provide an indication of air leak intensity based on the location of the computing device 470 relative to the user interface 424. Thus, as the user 410 maneuvers the computing device 470 along a path relative to the user interface 424, the user 410 can visually identify when the air leak meter 484 increases or decreases, thus facilitating identification of the location of the air leak (e.g., the air leak meter 484 will be higher when close to the air leak, and lower when further from the air leak).

In some cases, the computing device 470 can provide other feedback regarding the location of the air leak. For example, the computing device 470 can control lights or display devices to provide visual cues indicative of the location of the air leak. In some cases, the computing device 470 can provide haptic feedback, such as in the form of increasing or decreasing vibrations 488, or vibrations 488 of varying patterns, to provide an indication of the location and/or intensity of the air leak. In some cases, the computing device 470 can provide audio feedback, such as in the form of a tone of increasing and decreasing pitch, or computer-generated speech, to provide an indication of the location and/or intensity of the air leak. In some cases, the computing device 470 can present a visual annotation in the form of text to indicate the location (e.g., a textual description) and/or intensity (e.g., a numerical or enumerated scale) of the air leak.

In some cases, additional annotations (not shown) can be provided on the display 480 to provide feedback to the user 410 regarding where and/or how to move the computing device 470. For example, an arrow pointing towards the edge of the display 480 can be moved as appropriate to guide the user 410 in moving the computing device 470 along a desired path (e.g., a figure-8 path). In some cases, additional annotations can be provided to instruct the user 410 to perform certain actions designed to facilitate detection of the air leak. In an example, instructions can be provided to set the respiratory therapy device (e.g., respiratory therapy device 122 of FIG. 1) to a particular setting for the duration of the air leak test. In another example, instructions can be provided to make an adjustment to the user interface 424 to induce, increase, or decrease the air leak, to facilitate identification of the air leak and/or identification of the location of the air leak by the system.

In some cases, the display 480 can include a button 486 that can cause guidance to be shown. Guidance can provide information about how to improve fit of the user interface 424 and/or minimize air leaks. Guidance can be shown as text, images, and/or annotations. In some cases, annotations can be overlaid on image data (e.g., a live or delayed image or video of the user), such as to indicate how to adjust the user interface 424 to minimize air leaks. In some cases, guidance can be shown separate from the image data.

FIG. 5 is a user's view of a computing device 570 depicting fitting guidance, according to certain aspects of the present disclosure. The computing device 570 can be computing device 470 of FIG. 4 after pressing the button 487 to initiate guidance. As depicted in FIG. 5, the display device 572 presents a display 580 (e.g., a graphical user interface) that shows an image of a user interface 524 and includes annotations directing the user how to adjust the user interface 524 to improve fit and/or minimize air leak. While guidance may often be based on making adjustments to the user interface 524, that need not always be the case. In some cases, guidance can include guidance related to other aspects, such as the user 510 (e.g., instructions to remove hair between the user interface 524 and the user's face), the respiratory therapy device (e.g., instructions to adjust a flow rate), the conduit (e.g., instructions to adjust the conduit), and the like.

Any suitable annotation technique can be used. For example, text annotation 590 is a textual annotation that provides textual instructions for how to adjust the user interface 524. Text annotation 590 of FIG. 5 refers to tightening an indicated strap, although other text annotations may give more specific instructions.

In another example, arrow annotation 594 is a visual annotation that presents an arrow indicating that the strap near the arrow should be adjusted as shown by the arrow (e.g., tightened). In another example, highlighting annotation 592 is a visual annotation that highlights the strap or other part to be adjusted. Highlighting the strap or other part to be adjusted can include any technique for calling visual attention to the strap or other part to be adjusted, depicted in FIG. 5 as bold lines, for illustrative purposes.

In some cases, the display 580 can show a generic version of a user interface 524. However, in some cases, the display 580 can show the same type and/or model of user interface 524 that the user 510 is wearing (e.g., user interface 324 as seen in FIG. 3). In some cases, the actual guidance provided can also be tailored to the type and/or model of the user interface 524 that the user 510 is wearing. The type and/or model of user interface used for guidance (e.g., for displaying guidance and/or for the actual guidance provided) can be based on user interface identification information (e.g., a model number, a serial number, or the like).

User interface identification information can be actively provided by the user 510 (e.g., via an input interface, such as by the user typing in a model number or clicking on a model number), can be retrieved from storage (e.g., retrieved from storage of the respiratory therapy system 120 of FIG. 1, such as storage associated with the respiratory therapy device 122 of FIG. 1, or from storage of the computing device 570 from a previous use), or can be obtained dynamically. Obtaining user interface identification information dynamically can include using one or more sensors (e.g., one or more sensors of the computing device 570) to obtain the user interface identification information. In some cases, a camera can be used to read an encoded image associated with the user interface 524 (e.g., a QR code sticker on the user interface 524), which can be decoded to obtain the user interface identification information. In some cases, one or more sensors can be used to detect identifying features of the user interface 524 (e.g., unique shapes, patterns, or other visual elements, or combinations thereof), which can be used to determine the user interface identification information. For example, a camera (e.g., camera 450 of FIG. 4) can obtaining image data of the user interface (e.g., user interface 424 of FIG. 4) while it is being worn by user (e.g., user 410 of FIG. 4). Then, the computing device 470 can detect, from the image date, identifiable features of the user interface (e.g., size of the user interface, size and shape of vents, size and shape of conduit connection points, size and shape of straps, and/or any other elements), which the computing device 470 can use to determine user interface identification information associated with the user interface being worn by the user. Thus, the computing device 470 can provide guidance that is tailored to the specific user interface being worn by the user.

Computing device 570, while showing guidance, can nevertheless still use sensors (e.g., one or more microphones, camera 550, and the like) to continue detecting the location and/or intensity of the air leak.

In some cases, display 580 can include one or more annotations indicative of the location and/or intensity of the air leak. In some cases, it can be especially useful to provide an indication of the intensity of the air leak, so that as the user makes the indicated adjustments, the user can receive live feedback about whether or not the adjustments are reducing the air leak. For example, display 580 can include an air leak meter 584, similar to air leak meter 484 of FIG. 4. As the user makes the adjustments shown in the guidance, the air leak meter 484 may show a decrease in intensity of the air leak, thus indicating successful adjustments.

In some cases, the display 580 can include a button 586 that can cause the display 580 to show the captured image data (e.g., live images and/or video). For example, pressing button 586 may revert to the display 480 depicted in FIG. 4. In use, a user 510 may wish to switch back and forth between a camera display (e.g., as depicted in FIG. 4) and a guidance display (e.g., as depicted in FIG. 5). In some cases, a single display can provide a camera display and a guidance display without needing to switch between the two.

Figure 6:
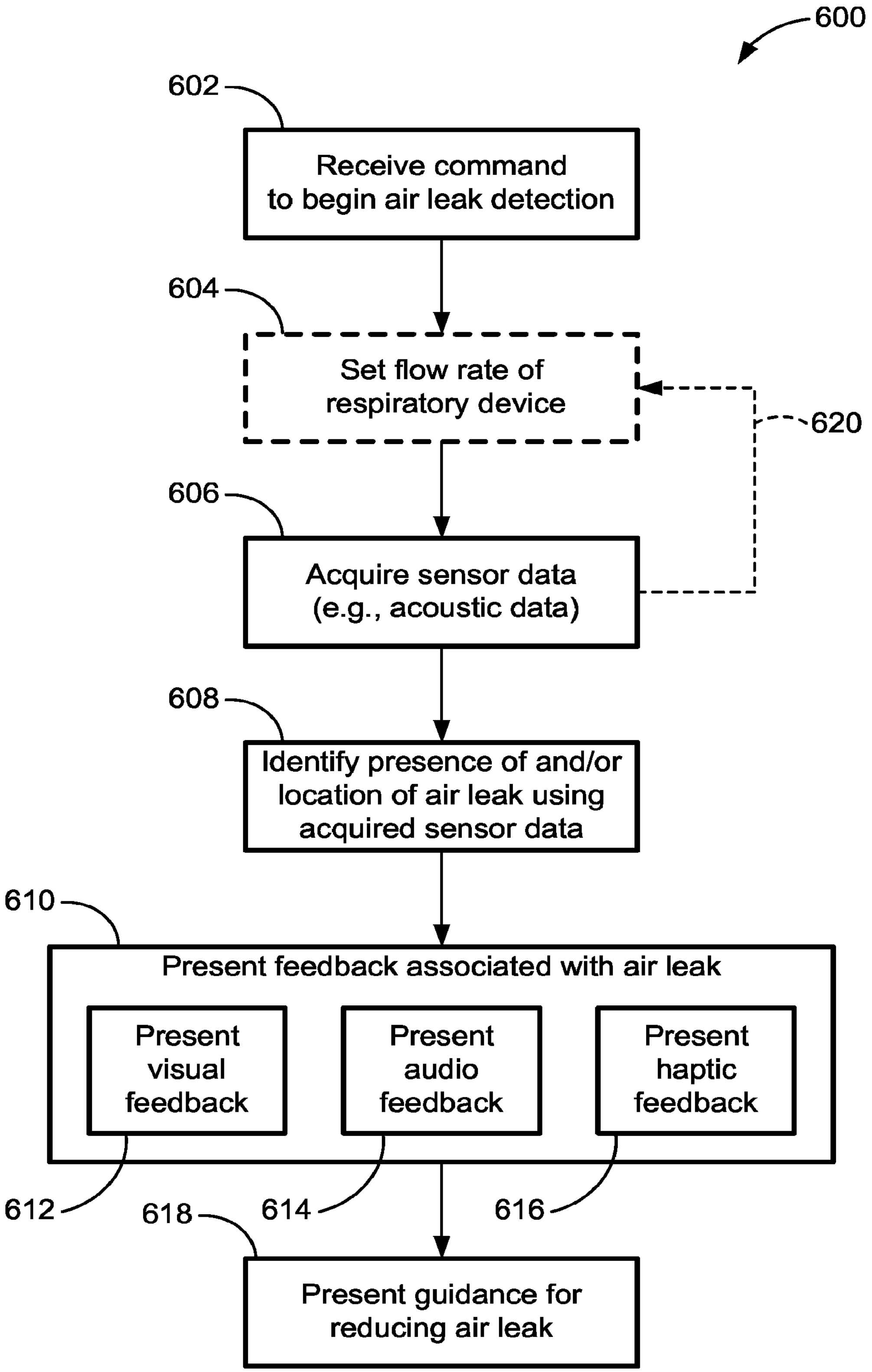
FIG. 6 is a flowchart depicting a process for identifying a leak in a user interface, according to certain aspects of the present disclosure.

FIG. 6 is a flowchart depicting a process 600 for identifying a leak in a user interface, according to certain aspects of the present disclosure. Process 600 can be performed by system 100 of FIG. 1. In some cases, process 600 can be performed by a computing device, such as a handheld computing device, such as a smartphone. Other devices can be used.

At block 602, a command is received to begin air leak detection. The command to begin air leak detection can be sent from a device of the system (e.g., from the respiratory therapy device 122 of FIG. 1 or an external device 170 of FIG. 1). In some cases, the command to begin air leak detection can be received at the external device 170 via user input acquired through an input interface. For example, a user may press a button on a computing device (e.g., a smartphone) to begin air leak detection, which causes the computing device to receive the command to begin air leak detection.

In some cases, at optional block 604, a flow rate of the respiratory therapy device can be set. Setting the flow rate at block 604 can include presenting an instruction on a display for a user to manually set a flow rate. In some cases, setting the flow rate at block 604 can include transmitting a flow rate command to a respiratory therapy device to set a flow rate of the respiratory therapy device. Setting the flow rate at block 604 can including setting the flow rate to a particular flow rate (e.g., a flow rate that achieves a pressure of 4 cm $H_2O$), setting the flow rate to a relative flow rate (e.g., lowering or raising the current flow rate), or setting the flow rate to a particular sequence of flow rates (e.g., a first flow rate for a certain duration or number of breaths, followed by a second flow rate). In some cases, instead of or in addition to setting a flow rate at block 604, other settings of the respiratory therapy device can be set.

At block 606, sensor data can be acquired. Acquiring sensor data at block 606 can include acquiring sensor data from one or more sensors (e.g., one or more sensors 130 of FIG. 1). In some cases, acquiring sensor data at block 606 can include acquiring acoustic data, such as from one or more microphones. Acquiring sensor data at block 606 can include receiving sensor data from one or more sensors and/or one or more devices of the system. For example, a smartphone performing process 600 can receive acoustic data from internal microphones, can receive additional acoustic data from wirelessly coupled microphones (e.g., in wireless headphones), and can receive pressure data from a wirelessly coupled respiratory therapy device. In this example, the acoustic data, additional acoustic data, and pressure data can be used to facilitate identifying the presence of and/or location of an unintentional air leak (e.g., at block 608).

In some cases, sensor data acquired at block 606 can be acquired as one or more sensors are being moved relative to the user interface, although that need not always be the case.

In some cases, a portion of the sensor data acquired at block 606 can be used to help process (e.g., filter and/or analyze) the remainder of the sensor data. For example, a portion of the sensor data acquired while the user is breathing can be used to identify intentional air leaks (e.g., venting) and/or other noises associated with normal user of the user interface, which can then be used in the processing of other sensor data to identify an unintentional air leak. For example, sensor noise associated with an intentional air leak can be filtered out of other sensor data to facilitate identifying an unintentional air leak in the other sensor data.

In some cases, setting a flow rate at block 604 and acquiring sensor data at block 606 can be repeated, as indicated by arrow 620. In such cases, one instance of setting the flow rate at block 604 and acquiring sensor data at block 606 may be used to acquire sensor data when the presence of any air leak is minimized due to use of a lower flow rate, while another instance of setting the flow rate at block 604 and acquiring sensor data at block 606 may be used to acquire additional sensor data when the presence of any air leak is not minimized due to use of a higher flow rate. In some cases, sensor data can be first acquired at the lower flow rate, although that need not always be the case. In such cases, the sensor data associated with the lower flow rate may include primarily sensor data associated with intentional air leaks and other noise of the user interface, whereas the sensor data associated with the higher flow rate may also include sensor data associated with any unintentional air leaks. As flow rate decreases, the pressure within the user interface decreases, resulting in less turbulence being generated from an unintentional air leak. Thus, sensor data acquired at a lower flow rate can be used to improve the processing (e.g., filtering and/or analysis) of sensor data acquired at a higher flow rate, thus facilitating identifying sensor data associated with the unintentional air leak. In some cases, the lower flow rate can be selected to achieve pressures at or less than 3 cm $H_2O$, whereas the higher flow rate can be selected to achieve pressures at or greater than 4 cm $H_2O$. Other flow rates can be used.

At block 608, acquired sensor data can be used to identify the presence of and/or location of an air leak (e.g., an unintentional air leak). As disclosed herein, various sensor data can be analyzed to determine whether or not an air leak is present, and/or a location of an air leak. For example, acquired acoustic data from a single microphone moving relative to a user interface can be used to identify a region of the user interface where the sounds associated with an air leak are the strongest, thus identifying the presence of (e.g., existence of) the air leak and an approximate location of the air leak. In another example, acquired acoustic data, image data, and depth data can be used in combination to generate a 2D and/or 3D mapping of the user interface and pinpoint a location of the air leak on the mapping.

At block 610, feedback associated with the air leak can be presented. The feedback can take the form of visual, audio, or haptic feedback, or any other suitable type of feedback. The feedback can be indicative of the presence of and/or location of the air leak. For example, feedback can be indicative of presence of an air leak, such as by displaying a text box on a display that reads either "Air Leak Detected" or "No Air Leaks Detected." In another example, feedback can be indicative of a relative location of an air leak, such as by providing increasing vibrations as the sensed intensity of the air leak increases (e.g., as the one or more sensors move closer to the air leak). In another example, feedback can be indicative of a specific location of an air leak, such as by providing an icon or annotation at a location on an image of the user interface that corresponds to the location of the air leak.

In some cases, at block 612, presenting feedback can include presenting visual feedback. Presenting visual feedback can include presenting a visual element on a display, such as presenting text or icons on a screen. In some cases, annotations can be presented on a display, such as overlaid on an image. In some cases, annotations can be overlaid on a live or delayed image of the user interface (e.g., a live image of the user wearing the user interface). In some cases, presenting visual feedback can include generating a visual cue using a light, such as a light emitting diode (LED) or other illumination device. Other visual feedback techniques can be used.

In some cases, at block 614, presenting feedback can include presenting audio feedback. Presenting audio feedback can include generating an audible sound, such as from a speaker. In an example, as a user moves one or more sensors (e.g., within a computing device) with respect to the user interface, a tone can change in frequency or volume as the one or more sensors come near the air leak. Thus, the air leak can be more easily identified by the user based on the audio feedback. Other audio feedback techniques can be used.

In some cases, at block 616, presenting feedback can include presenting haptic feedback. Presenting haptic feedback can include generating a tactile sensation, such as using a vibration motor or solenoid. In an example, as a user moves one or more sensors (e.g., within a computing device) with respect to the user interface, a vibration can be generated that can change in pattern or intensity as the one or more sensors come near the air leak. Thus, the air leak can be more easily identified by the user based on the haptic feedback. Other haptic feedback techniques can be used.

In some cases, guidance can be optionally presented for reducing the air leak at block 618. Presenting guidance at block 618 can include generating a visual display and/or providing audio instruction, although other guidance can be provided. The guidance presented at block 618 can include directions to make alterations to the user interface (e.g., adjusting a strap or sealing material such as a cushion of the user interface), to interact with the user interface in some fashion (e.g., pressing or pulling on a certain region of the user interface), to repair or replace a portion of the system (e.g., the user interface or a sealing material), or to take any other suitable action (e.g., to remove facial hair affecting the seal of the user interface to the user's face).

Guidance presented at block 618 can be based on the identified location of the air leak. For example, an air leak identified to be located in a first region of the user interface may lead to guidance to pull tight a first strap of the user interface, whereas an air leak identified to be located in a second region of the user interface may lead to guidance to pull tight a second strap of the user interface. In some cases, guidance can be based on the sensor data acquired at block 606. For example, characteristics of the air leak can be identified using the sensor data, and the identified characteristics can be used to tailor the guidance provided at block 618. In an example, acoustic characteristics of the air leak can be used to identify that the air leak is due to wear over time, rather than due to an inadvertently ill-fitting user interface (e.g., from a loose strap). In this example, the guidance can recommend replacing the user interface rather than simply recommending tightening a particular strap. Guidance can be otherwise tailored as disclosed herein.

Figure 7:
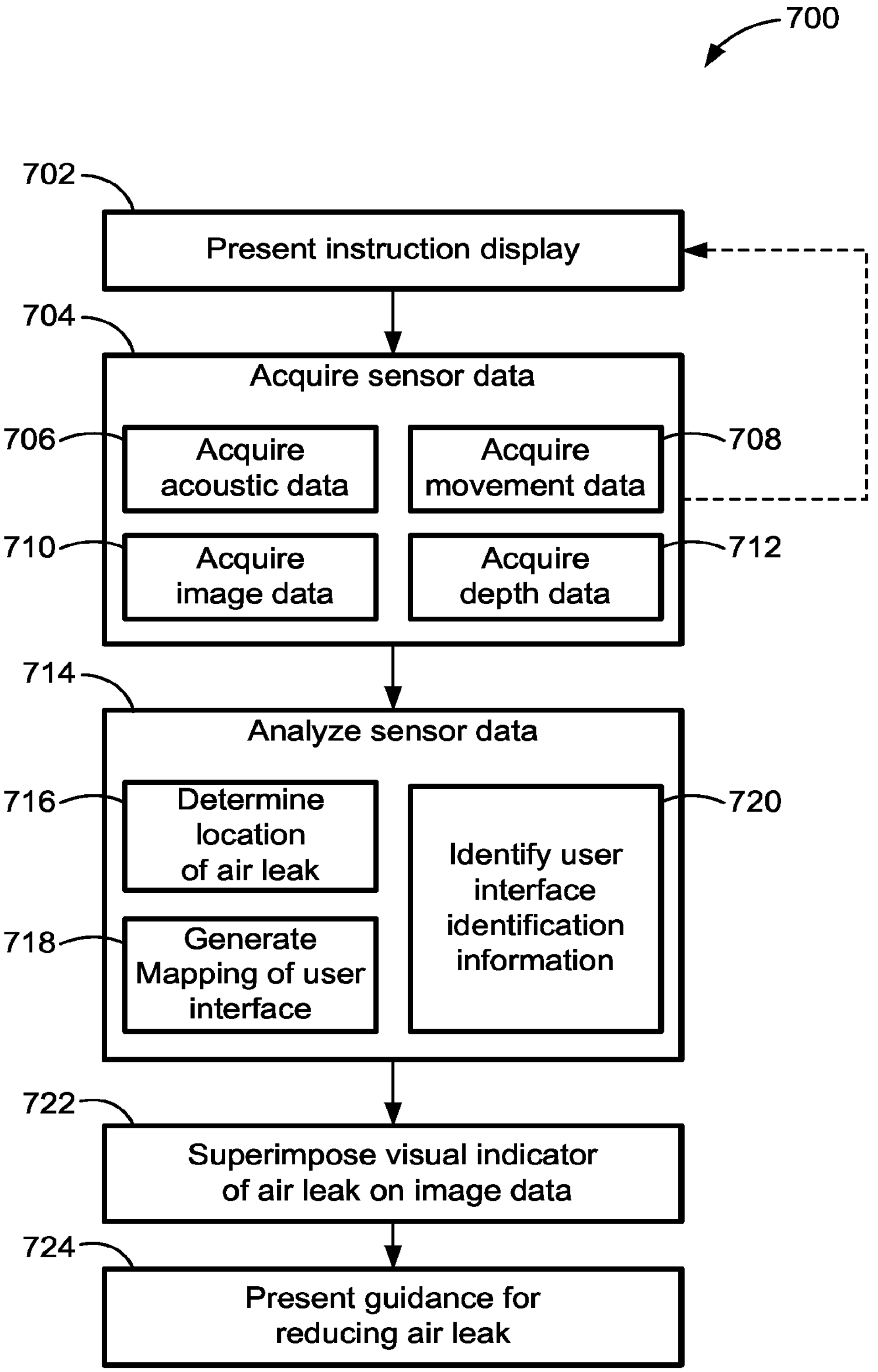
FIG. 7 is a flowchart depicting a process for identifying a leak in a user interface and presenting fitting guidance, according to certain aspects of the present disclosure.

FIG. 7 is a flowchart depicting a process 700 for identifying a leak in a user interface and presenting fitting guidance, according to certain aspects of the present disclosure. Process 700 can be performed by system 100 of FIG. 1. In some cases, process 700 can be performed by a computing device, such as a handheld computing device, such as a smartphone. Other devices can be used.

At block 702, an instruction display can be presented to a user. The instruction display can indicate how the user is to hold and/or manipulate the one or more sensors (e.g., one or more sensors 130 of FIG. 1, such as one or more sensors within a computing device). For example, the instruction display can provide an indication that a handheld computing device (e.g., smartphone) is to be maneuvered in a figure-8 pattern in front of a user interface being worn by the user. In some cases, presenting the instruction display can include presenting dynamic instructions for how to hold and/or manipulate the one or more sensors, such as an arrow pointing in the direction the one or more sensors should be moved. For example, dynamic instructions can take the form of an arrow that moves around an edge of a graphical user interface being displayed on a smartphone, pointing in the direction the user is to move the smartphone. The instruction display can include other instructions, such as how to orient the one or more sensors (e.g., keep the smartphone facing the same direction and within a plane perpendicular to a line extending out from the user's nose). Any suitable instructions can be provided in the instruction display. In some cases, instead of or in addition to providing an instruction display at block 702, instructions can be provided through another technique, such as audio instructions.

In some cases, the instruction display can include instructions to perform an action that may induce, increase, or decease an air leak. For example, instructions may be provided to push or pull on the user interface in a fashion that may induce an air leak or increase an existing air leak. While such action may appear counterproductive, it may facilitate overall reduction in air leaks, such as by facilitating the determination of the location of the air leak, especially for small air leaks that may otherwise be undetectable or difficult to detect. For example, a system uses a microphone that is not especially sensitive to higher frequencies, increasing an existing air leak may facilitate detecting the location of the air leak (e.g., since larger air leaks may exhibit acoustic patterns in lower frequencies), which can permit that temporarily increased air leak to be inevitably reduced and/or eliminated through corrective action.

At block 704 sensor data can be acquired. Acquiring sensor data can be the same as acquiring sensor data at block 606 of FIG. 6. Acquiring sensor data at block 704 can occur as the one or more sensors are being positioned and/or manipulated as instructed at block 702. In some cases, acquiring sensor data can include acquiring acoustic data at block 706, acquiring movement data at block 708, acquiring image data at block 710, acquiring depth data at block 712, acquiring any other suitable data, or any combination thereof.

Acquiring acoustic data at block 706 can include acquiring acoustic data from one or more microphones (e.g., microphone 140 of FIG. 1). Acquiring movement data (e.g., motion data) at block 708 can include acquiring data related to movement of the one or more sensors relative the user interface, including position information, orientation information, and the like, from any suitable sensor (e.g., motion sensor 138 of FIG. 1). In an example, accelerometer data, optionally with gyroscope data, can be used to estimate a relative path of movement of the one or more sensors, although other techniques can be employed to obtain movement data. Acquiring image data at block 710 can include acquiring still images and/or video from a camera (e.g., camera 150 of FIG. 1) or other image sensor (e.g., infrared sensor 152 of FIG. 1). In some cases, acquiring movement data at block 708 can include acquiring acoustic data and/or acquiring image data, which can be used to facilitate determining movement of the one or more sensors relative to the user interface. For example, analysis of image data from a rear-facing camera of a smartphone can help determine whether or not the user is maneuvering the smartphone in a figure-8 pattern as instructed. Acquiring depth data at block 712 can include acquiring data related to distances between the one or more sensors and the user interface, distances between different points of the user interface, and/or any other suitable distances. Acquiring depth data can include using any suitable sensor, such as a LiDAR sensor (e.g., LiDAR sensor 178 of FIG. 1), a set of cameras (e.g., multiple cameras 150 of FIG. 1), an infrared sensor (e.g., infrared sensor 152 of FIG. 1), a RF sensor (e.g., RF sensor 147 of FIG. 1), or the like. In some cases, acquiring depth data can include acquiring acoustic data, movement data, and/or image data. For example, movement data combined with acoustic data can be indicative of distances between the one or more sensors and different points of the user interface.

At block 714, the sensor data acquired at block 704 can be analyzed. The sensor data can be analyzed in real-time or near-real-time to provide information associated with the one or more sensors, information associated with the user interface, and/or information associated with an air leak. In some cases, at block 716, analysis of the sensor data can be used to determine a location of an air leak. Determining the location of the air leak can be similar to block 608 of FIG. 6. Determining the location of the air leak can be performed as otherwise disclosed herein.

In some cases, sensor data can be analyzed at block 714 to determine whether or not the one or more sensors are being manipulated properly according to the instructions presented at block 702. In some cases, analyzed sensor data from block 714 can be used at block 702 to present updated instructions. For example, if a user begins to move a smartphone away from the instructed path, the analyzed sensor data from block 714 may indicate this straying movement, causing the instructions presented at block 702 to update to show how the user must move the smartphone in order to return to or remain on the instructed path.

In some cases, analysis of the sensor data at block 714 can include generating a mapping of the user interface at block 718. Generating a mapping of the user interface at block 718 can include generating a 2-dimensional or 3-dimensional point cloud associated with the user interface. This mapping can be used to pinpoint a location of an air leak with respect to the user interface. In some cases, this mapping can be used to help identify user interface identification information of the user interface. In some cases, generating a mapping of the user interface can include generating a mapping of a portion of the user, such as a portion of the user supporting the user interface (e.g., the nose, face, and/head of the user).

In some cases, analysis of the sensor data at block 714 can include identifying user interface identification information using the sensor data. Identifying user interface identification information can include identifying any information usable to determine a manufacturer, type, or model of user interface. In some cases, identifying user interface identification information can include analyzing image data, such as to decode an encoded image (e.g., QR code) or identify a unique visual pattern associated with the user interface (e.g., a unique number of straps, a unique vent placement, unique coloring, or the like). In some cases, identifying user interface identification information can include using the mapping generated at block 718 and matching the mapping to a set of known user interfaces. In some cases, other sensor data can be used to identify user interface identification information. For example, a unique radio frequency identification (RFID) signal, a unique acoustic fingerprint (e.g., pattern of frequency peaks), or other recognizable signals can be received as sensor data and used to identify user interface identification information. Such signals (e.g., identification signals) can be transmitted from the user interface or an element associated with the user interface. In some cases, identification signals can be discernable to a user (e.g., a visual marking on a user interface), although that need not always be the case. In some cases, identification signals can be indiscernible to a user (e.g., an ultrasonic acoustic pattern or an RFID signal, which cannot be sensed by a user without the use of supplemental equipment).

In some cases, after analyzing sensor data at block 714, feedback can be provided to the user, such as disclosed with reference to block 610 of FIG. 6. For illustrative purposes, FIG. 7 is depicted with blocks 722 and 724, although one or both of blocks 722 and 724 can be removed, and other blocks can be used, as well.

At block 722, a visual indicator of the air leak can be superimposed on image data acquired at block 710. The visual indicator can be similar to air leak annotation 482 of FIG. 4. The location of the visual indicator can be based on the determined location of the air leak at block 716. In some cases, the location of the visual indicator can be further based on the mapping generated at block 718 and/or the identified user interface identification information from block 720 (e.g., known dimensions and/or locations of common air leaks for a particular user interface can be used to help pinpoint where the air leak is located, and thus where the air leak should be displayed on the image data). In some case, the visual indicator can include an indication of intensity of the air leak.

At block 724, guidance can be presented for reducing the air leak. Presenting guidance at block 724 can be similar to presenting guidance at block 618 of FIG. 6. The guidance presented at block 724 can be based on the location of the air leak from block 716. Presenting guidance at block 724 can include making use of the mapping from block 718 and/or the identified user interface identification information from block 720. For example, guidance presented at block 724 can be tailored to the location of the air leak, and optionally tailored to the shape or features of the user interface (e.g., as determined from the mapping from block 718 and/or the user interface identification information from block 720) and/or the shape or features of the user (e.g., a shape or features of the user as mapped along with the user interface at block 718).

FIG. 8 is a flowchart depicting a process 800 for calibrating sensor data for identifying a leak in a user interface and presenting guidance, according to certain aspects of the present disclosure. Process 800 can be performed by system 100 of FIG. 1. In some cases, process 800 can be performed by a computing device, such as a handheld computing device, such as a smartphone. Other devices can be used.

At block 802, device identification information can be determined. Device identification information can include identification information for one or more devices that include the one or more sensors (e.g., one or more sensors 130 of FIG. 1) used to acquire sensor data. Device identification information can be usable to identify a manufacturer, type and optionally model, or other information associated with a device that includes the one or more sensors. In an example, device identification information can include a model number of a smartphone containing the camera(s) and microphone(s) used to obtain sensor data for identifying an air leak.

Determining device identification information at block 802 can include determining sensor information about the one or more sensors used to detect the air leak. For example, knowledge of a model number for a smartphone may be used to determine the types of sensors and specifications of the sensors incorporated within the smartphone. In this example, if the particular model of smartphone being used includes microphones capable of detecting near-ultrasonic sound, the processes used to identify air leaks can take advantage of this capability to identify smaller air leak, optionally by adjusting how the sensor data can be processed (e.g., filtered and/or analyzed). In some cases, determining device identification information at block 802 can include determining sensor information, such as identification information of the sensor (e.g., a type and/or model of sensor) or specification information of the sensor (e.g., a frequency range or frequency sensitivity profile).

At block 804, sensor data can be acquired. Acquiring sensor data at block 804 can be similar to acquiring sensor data at blocks 606 and 704 of FIGS. 6 and 7, respectively. In some cases, acquiring sensor data at block 804 can include selecting what sensor data to acquire, which can include using the device identification information determined at block 802. In some cases, acquiring sensor data at block 804 can using the device identification information determined at block 802 (e.g., sensor specification information) to calibrate how the one or more sensors acquire data (e.g., adjusting gain or other properties of a sensor).

At optional block 806, sensor data from block 804 can be calibrated based on the device identification information from block 802. Calibrating sensor data can comprise making adjustments to live or stored sensor data based on the device identification information. For example, knowledge of certain specifications of a sensor (e.g., frequency sensitivity profile) can be used to calibrate (e.g., normalize) incoming sensor data. In some cases, calibrating sensor data at block 806 can facilitate obtaining consistent results regardless of what sensors are used. For example, calibrating sensor data at block 806 can facilitate consistent detection and/or localization of air leaks whether the user is using a smartphone alone, using the smartphone along with wireless headphones, or using an alternate device (e.g., a different type of computing device or another smartphone).

In some cases, sensor data from block 804 and/or calibrated sensor data from block 806 can be analyzed (e.g., analyzed as disclosed with reference to block 714 of FIG. 7).

In some cases, at block 808, the location of an air leak can be identified using the acquired, and optionally calibrated, sensor data. Identifying the location of the air leak at block 808 can be similar to determining the location of the air leak at block 716 of FIG. 7.

At block 810, guidance can be determined for reducing the air leak. This guidance can be determined based on the location of the air leak. In some cases, the guidance can optionally be further based on additional, optionally acquired sensor data. This additional, optionally acquired sensor data can refer to sensor data collected and used to determine information other than the location of the air leak. For example, sensor data used to identify a user interface (e.g., as disclosed with reference to block 720 of FIG. 7) can be optionally acquired, optionally calibrated, and used at block 810 to determine what guidance to give to the user. In some cases, determining guidance at block 810 can include using user-provided user interface information. User-provided user interface information can include information about the user interface (e.g., a manufacturer, type, model, or other identification information) that has been actively provided by the user. User-provided user interface information can be previously provided (e.g., previously provided in a set-up processes) or dynamically provided (e.g., provided in response to a current or recent prompt for user interface information). In some cases, user-provided user interface information can be obtained through a communicatively coupled device within the system, such as a respiratory therapy device.

At block 812, the guidance determined at block 810 can be presented. Presenting guidance can include presenting guidance in any suitable format, such as visually, audibly, or through any other suitable technique. In some cases, presenting guidance at block 812 can include presenting guidance images and/or instructions at block 814. Guidance images and/or instructions can include directions for steps the user should take to reduce, minimize, or eliminate the air leak. In some cases, guidance images and/or instructions can be user interface agnostic (e.g., generic instructions) or can be user interface specific (e.g., tailored to the type and/or model of user interface worn by the user). In some cases, presenting guidance at block 812 can include presenting a guidance image as an overlay on image data at block 816. For example, a guidance image in the form of an arrow or highlighting can be superimposed on image data (e.g., live image data from a camera feed) to indicate how a particular strap of the user interface is to be tightened or loosened. Any suitable guidance images can be displayed. In some cases, a guidance image can take the form of text. In some cases, a guidance image can take the form of arrows, highlighting, or other annotations. In some cases, a guidance image can take the form of a 2D or 3D model of an object, such as the user interface.

In some cases, at block 816, the system can provide feedback on guidance compliance. Feedback on guidance compliance can be based on continued acquisition and analysis of sensor data (e.g., blocks 804, 806, 808). For example, feedback on guidance compliance can be shown as a reduction in an intensity of or elimination of an air leak. In some cases, feedback on guidance compliance can be provided dynamically as the user is adjusting the user interface. In such cases, the user can use the feedback on guidance compliance to easily determine how much to adjust the user interface and/or whether further adjustments are needed. For example, guidance to pull on a strap of the user interface can lead a user to begin pulling on that strap and continue pulling on the strap until the feedback presented to the user indicates that the air leak has ceased.

In some cases, feedback on guidance compliance can include further iterations of blocks 808, 810, and/or 812). In such cases, feedback on guidance compliance can include information about how to further adjust the user interface and/or other elements to further reduce the air leak and/or reduce one or more additional air leaks that may have been created in response to the initial guidance. Thus, blocks 804, 806, 808, 810, 812, and/or 816 can be performed iteratively and/or continually until proper fit has been achieved.

While the blocks of processes 600, 700, and 800 are depicted with arrows, it will be understood that various blocks can occur simultaneously and/or continuously, as well as in other orders than as depicted in FIGS. 7-8. Further, while specific collections of blocks within processes 600, 700, and 800 are depicted for illustrative purposes, various blocks can be used in other processes, as appropriate. For example, while setting a flow rate is described with reference to block 604 in FIG. 6, flow rates can be similarly set when acquiring sensor data at blocks 704 and 804 of FIGS. 7 and 8, respectively.

Figure 9:
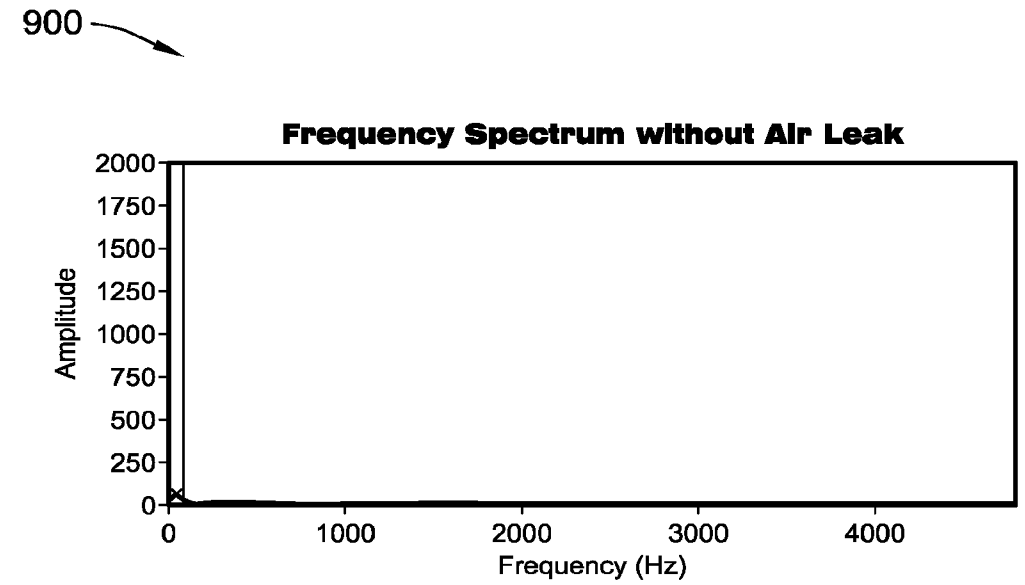
FIG. 9 is a chart depicting frequency response of detected acoustic signals for a user interface without an air leak, according to certain aspects of the present disclosure.

FIG. 9 is a chart 900 depicting frequency response of detected acoustic signals for a user interface without an air leak, according to certain aspects of the present disclosure. The acoustic signals depicted in chart 900 can be acoustic data from one or more sensors (e.g., one or more sensors 130 of FIG. 1), such as a microphone of a smartphone. Chart 900 depicts the intensity of various frequencies of the acoustic signal for a user receiving respiratory therapy via a user interface at a pressure of 4 cm $H_2O$, such as described with reference to system 100 of FIG. 1. In the example depicted in chart 900, no unintentional air leaks are present, and thus the only frequency peaks in the acoustic signal are near the low end (e.g., around 50-60 Hz). In some cases, the frequency response seen in chart 900 can be used as a baseline to filter out intentional air leaks and/or noise associated with a user interface.

Figure 10:
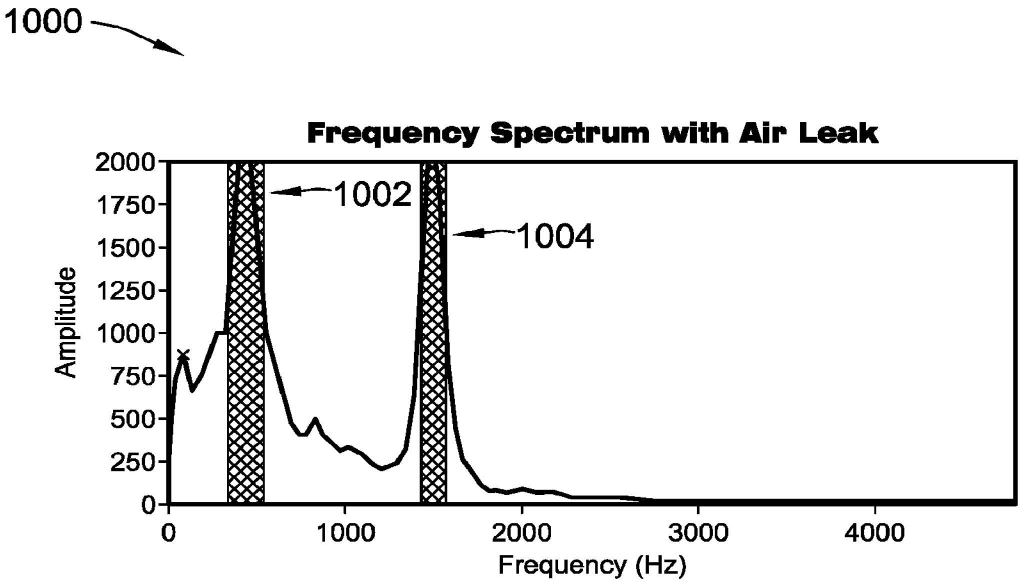
FIG. 10 is a chart depicting frequency response of detected acoustic signals for a user interface exhibiting an air leak, according to certain aspects of the present disclosure.

FIG. 10 is a chart 1000 depicting frequency response of detected acoustic signals for a user interface exhibiting an air leak, according to certain aspects of the present disclosure. The acoustic signals depicted in chart 1000 can be acoustic data from one or more sensors (e.g., one or more sensors 130 of FIG. 1), such as a microphone of a smartphone. Chart 1000 depicts the intensity of various frequencies of the acoustic signal for a user receiving respiratory therapy via a user interface at a pressure of 4 cm $H_2O$, such as described with reference to system 100 of FIG. 1. The setup used to generate the acoustic signals for chart 1000 can be identical to the setup used to generate the acoustic signals for chart 900, except with the presence of an unintentional air leak.

In the example depicted in chart 1000, an unintentional air leak is present, and thus additional frequency peaks are depicted in the acoustic signal. The additional frequency peaks can be due to the sound created from turbulence induced by air flow associated with an air leak. As seen in chart 1000, these additional frequency peaks occur at location 1002 and location 1004, corresponding to at or around 100 Hz and at or around 1000 Hz. As depicted in the example in chart 1000, the presence of localized frequency peaks within windows (e.g., a 5%, 6%, 7%, 8%, 9%, and/or 10% window) surrounding 100 Hz and 1000 Hz can be used as an indication that the sound is caused by an unintentional air leak. Thus, presence of similar peaks in a detected acoustic signal can be indicative of the existence of an unintentional air leak. By maneuvering the microphone around the user interface, the location of the unintentional air leak can be estimated as being near where the microphone is located when the amplitude of the peaks at locations 1002 and 1004 are at their highest. In some cases, as disclosed in further detail herein, the acoustic data signals from multiple microphones located at different positions or from one or more microphones moved through different positions can be used to pinpoint a location (e.g., via triangulation or beamforming) of the air leak.

In some cases, instead of identifying an air leak by specific frequency thresholds, an unintentional air leak can be identified by a spectral shape or pattern that is differentiable from noise associated with intentional air leaks or other expected noises. In some cases, the acoustic signal can be processed to determine the existence of an unintentional air leak by processing the acoustic signal through a learned algorithm or comparing the acoustic signal to known spectral shapes or patterns of known unintentional air leaks. For example, some types of unintentional air leak may have peaks at locations other than 100 Hz and 1000 Hz, but may exhibit a recognizable spectral shape or pattern outside of the 50-60 Hz range associated with normal operation of the respiratory therapy device. While the spectral peaks at 100 Hz and 1000 Hz is used as an example in FIG. 10, other peaks can be used to detect other types of unintentional air leaks.

Also depicted in chart 1000, the relatively smaller localized peak around 50-60 Hz can be used to determine a relative intensity of the unintentional air leaks and/or other noise associated with using the user interface. Thus, an overall intensity of the air leak can be determined based on the overall intensity of the recognized frequencies (e.g., frequency peaks at locations 1002 and 1004) and a relative intensity of the air leak with respect to the unintentional air leak and/or other user interface noises can be determined based on a comparison between the peak at around 50-60 Hz and the peaks at locations 1002 and 1004.

One or more elements or aspects or steps, or any portion(s) thereof, from one or more of any of the claims listed below can be combined with one or more elements or aspects or steps, or any portion(s) thereof, from one or more of any of the other claims listed below or combinations thereof, to form one or more additional implementations and/or claims of the present disclosure.

The foregoing description of the embodiments, including illustrated embodiments, has been presented only for the purpose of illustration and description and is not intended to be exhaustive or limiting to the precise forms disclosed. Numerous modifications, adaptations, and uses thereof will be apparent to those skilled in the art.

What is claimed is:

1. A method for detecting air leaks of a user interface worn by a user, comprising:

receiving, at a computing device, a command to begin air leak detection of the user interface being worn by the user;

responsive to receiving the command to begin air leak detection, transmitting from the computing device, a flow rate command to a respiratory therapy device coupled to the user interface;

responsive to receiving the flow rate command, causing the respiratory therapy device to operate at a sequence of flow rates having at least a first flow rate and a second flow rate, receiving, from one or more sensors, acoustic data generated at each of the first flow rate and the second flow rate, wherein the acoustic data at the first flow rate includes baseline acoustic data associated with intentional venting;

analyzing the acoustic data at the second flow rate by comparing the acoustic data at the first flow rate and the acoustic data at the second flow rate;

identifying a location of an air leak using the received acoustic data at the second flow rate after the comparing with the acoustic data at the first flow rate; and presenting an indicator that is indicative of the location of the identified air leak; and iteratively:

(i) prompting the user with guidance to adjust the user interface to reduce the air leak;

(ii) transmitting, from the computing device to the respiratory therapy device, an updated flow rate command based on the identified location of the air leak, the updated flow rate command causing the respiratory therapy device to operate at an adjusted flow rate;

(iii) receiving, from the one or more sensors, updated acoustic data while the respiratory therapy device operates at the adjusted flow rate; and (iv) determining, based on the updated acoustic data, whether an intensity of the air leak has been reduced, until the updated acoustic data indicates that the intensity of the air leak has been reduced.

2. The method of claim 1, wherein the identified air leak is an unintentional air leak.

3. The method of claim 1, further comprising receiving movement data associated with movement of the computing device relative the user interface, wherein identifying the location of the air leak uses the acoustic data and the movement data.

4. The method of claim 1, wherein identifying the location of the air leak comprises:

accessing the baseline acoustic data associated with intentional venting of the user interface; and filtering the baseline acoustic data to the acoustic data to identify the air leak.

5. The method of claim 1, wherein identifying the location of the air leak comprises:

analyzing the acoustic data to identify a spectral frequency characteristic associated with the air leak; and determining a relative strength of the air leak based on the spectral frequency characteristic.

6. The method of claim 1, further comprising presenting an instruction display, wherein the instruction display is indicative of a movement path for moving the computing device relative to the user interface.

7. The method of claim 6, wherein presenting the instruction display comprises presenting feedback associated with the accuracy of the computing device's movement along the movement path.

8. The method of claim 1, further comprising receiving depth data associated with a distance between the computing device and the user interface, wherein identifying a location of the air leak further comprises:

generating a three-dimensional mapping of the user interface relative to the computing device; and identifying the location of the air leak using the three-dimensional mapping of the user interface.

9. The method of claim 1, wherein the acoustic data is associated with acoustic signals between 20 Hz and 20 kHz.

10. The method of claim 1, further comprising receiving image data associated with the user interface, wherein presenting the indicator comprises presenting a visual indicator superimposed on the image data associated with the user interface.

11. The method of claim 10, wherein receiving the image data associated with the user interface comprises capturing the image data using a camera of the computing device and displaying the image data on a display of the computing device.

12. The method of claim 11, wherein the image data is live image data.

13. The method of claim 10, further comprising:

identifying the guidance for reducing the air leak based on the location of the air leak;

generating a guidance image based on the guidance for reducing the air leak; and presenting the guidance by superimposing the guidance image on the image data associated with the user interface.

14. The method of claim 13, further comprising determining user interface identification information based on the received image data, wherein the user interface identification information is usable to identify a manufacturer of the user interface, a type of the user interface, or a model of the user interface, or any combination thereof, and wherein identifying guidance for reducing the air leak is based on the user interface identification information.

15. The method of claim 1, further comprising:

determining device identification information associated with the computing device, wherein the device identification information is usable to identify a manufacturer of the computing device, a model of the computing device, or an identification of one or more sensors of the computing device, or any combination thereof; and calibrating the acoustic data based on the device identification information.

16. The method of claim 1, further comprising receiving image data associated with the user interface; and identifying a region of interest using the received image data, wherein identifying the location of the air leak using the received acoustic data further includes using the identified region of interest, and wherein identifying the region of interest using the received image data includes:

applying the image data to a comparison database to identify a matching user interface, the comparison database including a collection of geometric models of a range of user interfaces; and determining the region of interest using the matching user interface.

17. The method of claim 16, wherein identifying the location of the air leak using the received acoustic data and the identified region of interest includes identifying a portion of the received acoustic data associated with the region of interest and analyzing the portion of the received acoustic data to identify the air leak.

18. The method of claim 1, further comprising:

receiving image data associated with the user interface over a duration of time; and determining relative positions of a microphone with respect to the user interface during the duration of time using the image data, wherein the microphone is moved with respect to the user interface during the duration of time;

wherein receiving the acoustic data includes receiving the acoustic data from the microphone during the duration of time, and wherein identifying the location of the air leak using the received acoustic data further includes using the determined relative positions of the microphone with respect to the user interface.

19. The method of claim 18, wherein identifying the location of the air leak using the received acoustic data and the determined relative positions of the microphone with respect to the user interface includes:

identifying one or more dominant spectral components of an acoustic source from the acoustic data;

calculating an unwrapped phase of the one or more dominant spectral components over time;

determining distances between the microphone and the acoustic source using the unwrapped phase; and determining the location of the air leak with respect to the user interface using the determined distances between the microphone and the acoustic source and the relative positions of the microphone with respect to the user interface.

20. The method of claim 18, wherein identifying the location of the air leak using the received acoustic data and the determined relative positions of the microphone with respect to the user interface includes:

identifying a change in distance between the microphone and the user interface using the relative positions of the microphone with respect to the user interface over the duration of time;

determining a phase shift of an acoustic source during the duration of time using the received acoustic data;

determining a change in distance between the microphone and an acoustic source over the duration of time using the identified change in distance between the microphone and the user interface; and determining the location of the air leak using the determined phase shift, the determined change in distance between the microphone and the acoustic source over time, and a speed of sound.

21. A system comprising:

a control system including one or more processors; and a memory having stored thereon machine readable instructions;

wherein the control system is coupled to the memory, and the method of claim 1 is implemented when the machine executable instructions in the memory are executed by at least one of the one or more processors of the control system.

22. A computer program product embodied on a non-transitory computer readable medium, the computer-program product comprising instructions which, when executed by a computer, cause the computer to carry out the method of claim 1.

* * * * *